US007964344B2

(12) United States Patent
Suzuki et al.

(10) Patent No.: US 7,964,344 B2
(45) Date of Patent: Jun. 21, 2011

(54) STABLE HYBRID

(75) Inventors: Tomohiro Suzuki, Kanagawa (JP); Mie Ishii, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1653 days.

(21) Appl. No.: 10/939,597

(22) Filed: Sep. 14, 2004

(65) Prior Publication Data
US 2005/0059069 A1   Mar. 17, 2005

(30) Foreign Application Priority Data

Sep. 17, 2003 (JP) .................................. 2003-324647

(51) Int. Cl.
C12Q 1/68 (2006.01)
C07H 21/00 (2006.01)
C07H 21/02 (2006.01)
C07H 21/04 (2006.01)

(52) U.S. Cl. .......... 435/6; 536/22.1; 536/23.1; 536/24.3

(58) Field of Classification Search ..... 435/6; 536/23.1, 536/24.3
See application file for complete search history.

(56) References Cited

U.S. PATENT DOCUMENTS

| | | | | | |
|---|---|---|---|---|---|
| 4,775,619 | A | * | 10/1988 | Urdea | 435/6 |
| 5,532,128 | A | * | 7/1996 | Eggers et al. | 435/6 |
| 5,753,439 | A | * | 5/1998 | Smith et al. | 435/6 |
| 6,387,626 | B1 | * | 5/2002 | Shi et al. | 435/6 |
| 6,410,229 | B1 | | 6/2002 | Lockhart et al. | 435/6 |
| 6,468,476 | B1 | * | 10/2002 | Friend et al. | 422/68.1 |
| 6,537,759 | B1 | * | 3/2003 | Stanton, Jr. | 435/6 |
| 6,569,671 | B1 | | 5/2003 | Okamoto et al. | 435/285.1 |
| 6,593,091 | B2 | * | 7/2003 | Keys et al. | 435/6 |
| 6,664,051 | B1 | | 12/2003 | Shinoki et al. | 435/6 |
| 6,686,151 | B1 | * | 2/2004 | Lazar et al. | 435/6 |
| 6,686,439 | B2 | | 2/2004 | Kenmoku et al. | 528/272 |
| 6,737,238 | B2 | | 5/2004 | Suzuki et al. | 435/6 |
| 2001/0010910 | A1 | * | 8/2001 | Hyldig-Nielsen et al. | 435/6 |
| 2001/0055114 | A1 | | 12/2001 | Suzuki et al. | 356/317 |
| 2002/0045169 | A1 | * | 4/2002 | Shoemaker et al. | 435/6 |
| 2002/0068282 | A1 | | 6/2002 | Okamoto et al. | 435/6 |
| 2002/0115072 | A1 | | 8/2002 | Okamoto et al. | 435/6 |
| 2002/0197630 | A1 | * | 12/2002 | Knapp et al. | 435/6 |
| 2003/0059907 | A1 | | 3/2003 | Suzuki et al. | 435/135 |
| 2003/0087259 | A1 | * | 5/2003 | Clancy et al. | 435/6 |
| 2004/0241643 | A1 | | 12/2004 | Yamamoto et al. | 435/5 |
| 2008/0176757 | A1 | * | 7/2008 | Hassibi et al. | 506/9 |

FOREIGN PATENT DOCUMENTS

| | | |
|---|---|---|
| JP | 11-508122 A | 7/1999 |
| JP | 2001-128683 | 5/2001 |
| JP | 2006-507792 A | 3/2006 |
| WO | WO 95/11995 | 5/1995 |
| WO | 96/29431 A2 | 9/1996 |
| WO | WO 02/27026 | 4/2002 |
| WO | WO 02/38729 | 5/2002 |
| WO | 03/038042 A2 | 5/2003 |
| WO | 2004/031406 | 4/2004 |

OTHER PUBLICATIONS

Shumaker et al. Mutation detection by solid phase primer extension. Human Mutation 7:346-354 (1996).*
The Stratagene Catalog, p. 39 (1988).*
Pastinen et al., A system for specific, high-throughput genotyping by allele-specific primer extension. Genome Research 10 : 1031-1042 (2000).*
Burland et al., Long PCR facilitates concise cloning and sequencing with a minimal tiling set of templates. Biotechniques 23(6) : 1070-1075 (1997).*
Stimpson et al., Real-time detection of DNA hybridization and melting on oligonucleotide arrays by using optical wave guides. PNAS 92:6379-6383 (Jul. 1995).*
Pease et al. , Light-generated oligonucleotide arrays for rapid DNA sequence analysis. PNAS 91 : 5022-5026 (May 1994).*
Guo et al., Direct flurescence analysis of genetic polymorphisms by hybridization with oligonucleotide arrays on glass supports. Nucleic Acids Research 22(24) :5456-5465(1994).*
Culha et al., Application of a miniture biochip using the molecular beacon probe in breast cancer gene BRACA1 detection. Biosensors & Bioelectronics 19 : 1007-1012 (Apr. 15, 2004).*
Beaucage, Strategies in the preparation of DNA oligonucleotide Arrays for diagnostic applications. Current Medicinal Chemistry 8 : 1213-1244 (2001).*
Weiler et al., Hybridization based DNA screening on peptide nucleic acid (PNA) oligomer arrays. Nucleic Acids Research 25(14) : 2792-2799 (1997).*
Lai et al., Quantification of Substance P mRNA in human immune cells by real-time reverse transcriptase PCR assay. Clinical and Diagnostic Laboratory Immunology 9(1) : 138-143 (Jan. 2002).* Tyagi et al., Molecular Beacons : Probes that fluoresce upon hybridization. Nature Biotechnology 14 : 303-308 (1996).*
Tsourkas et al., Hybridization of 2'-O-methyl and 2'-deoxy molecul;ar beacons to RNA and DNA targets. Nucleic Acids Research 30(23) :5168-5174 (2002).*
Barlic-Maganja et al., Highly sensitive one-tube RT-PCR and microplate hybridization assay for the detection and for the discrimination of classical swine fever virus from other pestiviruses. J. of Virological Methods 95 : 101-110 (2001).*
Wang et al. Label-free hybridization detection of a single nucleotide mismatch by immobilization of molecular beacons on an agarose film. Nucleic Acids Research 30(12) e61 : 1-9 (2002).*
Belanger et al., Rapid detection of Shiga Toxin-producing bacteria in feces by multiplex PCR with molecular beacons on the smart cycler. Journal of Clinical Microbiology 40(4) : 1436-1440 (Apr. 2002).*
He et al., Detection and quantification of mitochondrial DNA deletions in individual cells by real-time PCR. Nucleic Acids Research 30(12) e61 : 1-9 (2002).*

(Continued)

Primary Examiner — Ethan Whisenant
(74) Attorney, Agent, or Firm — Fitzpatrick, Cella, Harper & Scinto

(57) ABSTRACT

A hybrid formed of a probe nucleic acid immobilized onto a substrate and a sample nucleic acid, in which the target strand of the sample nucleic acid is longer than the probe nucleic acid, so that at least a 5' end portion of the target strand extends upstream the target sequence; a 3' end of the target strand is the same as a 3' end of the target sequence or extends downstream the target sequence by at least one base from the 3' end of the target sequence; and provided that when the number of bases of the extending 5' portion is designated as L1, and the number of bases of the extending 3' portion of the target strand is designated as L2, a value of L1/L2 falls within the range of 0 to 1.5 both inclusive. This hybrid is very stable so that useful for detecting a small amount of nucleic acid specifically with high sensitivity.

2 Claims, 4 Drawing Sheets

OTHER PUBLICATIONS

Perlette et al. Real-time monitoring of intracellular mRNA hybridization inside single living cells. Analytical Chemistry 73 : 5544-5550 (2001).*

Tamiya et al., Two types of defective human T-lymphotopic virus type I provirus in adult T-cell leukemia. Blood 88 (8) : 3065-3073 (Oct. 1996).*

Cheng et al., Characterization of large CTG repeat expansions in myotonic dystrophy alleles using PCR. Human Mutation 7 : 304-310 (1996).*

Saiki et al. Genetic analysis of amplified DNA with immobilized sequence-specific oligonucleotide probes PNAS 86(16) : 6230-6234 (1989).*

Lawn et al. The nucleotide sequence of the Human β-globin gene Cell 21 : 647-651 (1980).*

M. Lopez, et al., "Fingerprinting of prokaryotic 16S rRNA genes using oligodeoxyribonucleotide microarrays and virtual hybridization," Nucleic Acids Research, vol. 31, No. 2, 2003, pp. 779-789.

A. Femino, et al., "Visualization of Single RNA Transcripts in Situ," Science, vol. 280, Apr. 24, 1998, pp. 585-590.

Ray, et al., "Peptide nucleic acid (PNA): its medical and biotechnical applications and promise for the future", The FASEB Journal, vol. 14, Jun. 2000, pp. 1041-1060.

* cited by examiner

25mer PROBE

40mer PROBE

60mer PROBE

25mer PROBE (3'THIOL)

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial
<220> FEATURE:
<223> OTHER INFORMATION: PCR primer F1

<400> SEQUENCE: 1
tgatttgggt gatggttcac gtag                                          24

<210> SEQ ID NO 2
<211> LENGTH: 22
<212> TYPE: DNA
<213> ORGANISM: Artificial
<220> FEATURE:
<223> OTHER INFORMATION: PCR primer F2

<400> SEQUENCE: 2
gagctgcatg tgtcagaggt tt                                            22

<210> SEQ ID NO 3
<211> LENGTH: 22
<212> TYPE: DNA
<213> ORGANISM: Artificial
<220> FEATURE:
<223> OTHER INFORMATION: PCR primer R1

<400> SEQUENCE: 3
atcagcaata aaccagccag cc                                            22

<210> SEQ ID NO 4
<211> LENGTH: 25
<212> TYPE: DNA
<213> ORGANISM: Artificial
<220> FEATURE:
<223> OTHER INFORMATION: Primer P1

<400> SEQUENCE: 4
atggtgcact ctcagtacaa tctgc                                         25

<210> SEQ ID NO 5
<211> LENGTH: 25
<212> TYPE: DNA
<213> ORGANISM: Artificial
<220> FEATURE:
<223> OTHER INFORMATION: Primer P2

<400> SEQUENCE: 5
gtgggttaca tcgaactgga tctca                                         25

<210> SEQ ID NO 6
```

```
<211> LENGTH: 25
<212> TYPE: DNA
<213> ORGANISM: Artificial
<220> FEATURE:
<223> OTHER INFORMATION: Primer P3

<400> SEQUENCE: 6
gataaagttg caggaccact tctgc                                         25

<210> SEQ ID NO 7
<211> LENGTH: 22
<212> TYPE: DNA
<213> ORGANISM: Artificial
<220> FEATURE:
<223> OTHER INFORMATION: Primer FP1

<400> SEQUENCE: 7
cttaatcgcc ttgcagcaca tc                                            22

<210> SEQ ID NO 8
<211> LENGTH: 24
<212> TYPE: DNA
<213> ORGANISM: Artificial
<220> FEATURE:
<223> OTHER INFORMATION: Primer FP2

<400> SEQUENCE: 8
tgatttgggt gatggttcac gtag                                          24

<210> SEQ ID NO 9
<211> LENGTH: 22
<212> TYPE: DNA
<213> ORGANISM: Artificial
<220> FEATURE:
<223> OTHER INFORMATION: Primer FP3

<400> SEQUENCE: 9
gagctgcatg tgtcagaggt tt                                            22

<210> SEQ ID NO 10
<211> LENGTH: 22
<212> TYPE: DNA
<213> ORGANISM: Artificial
<220> FEATURE:
<223> OTHER INFORMATION: Primer FP4

<400> SEQUENCE: 10
ttcttagacg tcaggtggca ct                                            22

<210> SEQ ID NO 11
<211> LENGTH: 22
<212> TYPE: DNA
<213> ORGANISM: Artificial
<220> FEATURE:
<223> OTHER INFORMATION: Primer FP5

<400> SEQUENCE: 11
ccttcctgtt tttgctcacc ca                                            22

<210> SEQ ID NO 12
<211> LENGTH: 22
<212> TYPE: DNA
<213> ORGANISM: Artificial
<220> FEATURE:
<223> OTHER INFORMATION: Primer, PF6

<400> SEQUENCE: 12
```

```
gcatcttacg gatggcatga ca                                              22

<210> SEQ ID NO 13
<211> LENGTH: 22
<212> TYPE: DNA
<213> ORGANISM: Artificial
<220> FEATURE:
<223> OTHER INFORMATION: Primer FP7

<400> SEQUENCE: 13
tgaagccata ccaaacgacg ag                                              22

<210> SEQ ID NO 14
<211> LENGTH: 22
<212> TYPE: DNA
<213> ORGANISM: Artificial
<220> FEATURE:
<223> OTHER INFORMATION: Primer FP8

<400> SEQUENCE: 14
ttactctagc ttcccggcaa ca                                              22

<210> SEQ ID NO 15
<211> LENGTH: 22
<212> TYPE: DNA
<213> ORGANISM: Artificial
<220> FEATURE:
<223> OTHER INFORMATION: Primer RP1

<400> SEQUENCE: 15
ttcggtgatg acggtgaaaa cc                                              22

<210> SEQ ID NO 16
<211> LENGTH: 24
<212> TYPE: DNA
<213> ORGANISM: Artificial
<220> FEATURE:
<223> OTHER INFORMATION: Primer RP2

<400> SEQUENCE: 16
actggtgagt actcaaccaa gtca                                            24

<210> SEQ ID NO 17
<211> LENGTH: 22
<212> TYPE: DNA
<213> ORGANISM: Artificial
<220> FEATURE:
<223> OTHER INFORMATION: Primer RP3

<400> SEQUENCE: 17
atcagcaata aaccagccag cc                                              22

<210> SEQ ID NO 18
<211> LENGTH: 21
<212> TYPE: DNA
<213> ORGANISM: Artificial
<220> FEATURE:
<223> OTHER INFORMATION: Primer RP4

<400> SEQUENCE: 18
tacgggaggg cttaccatct g                                               21

<210> SEQ ID NO 19
<211> LENGTH: 22
<212> TYPE: DNA
<213> ORGANISM: Artificial
<220> FEATURE:
```

```
<223> OTHER INFORMATION: Primer RP5

<400> SEQUENCE: 19
catccatagt tgcctgactc cc                                        22

<210> SEQ ID NO 20
<211> LENGTH: 22
<212> TYPE: DNA
<213> ORGANISM: Artificial
<220> FEATURE:
<223> OTHER INFORMATION: Primer RP6

<400> SEQUENCE: 20
acgctcagtg gaacgaaaac tc                                        22

<210> SEQ ID NO 21
<211> LENGTH: 22
<212> TYPE: DNA
<213> ORGANISM: Artificial
<220> FEATURE:
<223> OTHER INFORMATION: Primer RP7

<400> SEQUENCE: 21
gcgccttatc cggtaactat cg                                        22

<210> SEQ ID NO 22
<211> LENGTH: 25
<212> TYPE: DNA
<213> ORGANISM: Artificial
<220> FEATURE:
<223> OTHER INFORMATION: Probe A25

<400> SEQUENCE: 22
atggtgcact ctcagtacaa tctgg                                     25

<210> SEQ ID NO 23
<211> LENGTH: 25
<212> TYPE: DNA
<213> ORGANISM: Artificial
<220> FEATURE:
<223> OTHER INFORMATION: Probe B25

<400> SEQUENCE: 23
gtgggttaca tcgaactcga tctca                                     25

<210> SEQ ID NO 24
<211> LENGTH: 25
<212> TYPE: DNA
<213> ORGANISM: Artificial
<220> FEATURE:
<223> OTHER INFORMATION: Probe C25

<400> SEQUENCE: 24
gataaagttg caggaccact tctgc                                     25

<210> SEQ ID NO 25
<211> LENGTH: 40
<212> TYPE: DNA
<213> ORGANISM: Artificial
<220> FEATURE:
<223> OTHER INFORMATION: Probe A40

<400> SEQUENCE: 25
atggtgcact ctcagtacaa tctgctctga tgccgcatag                     40

<210> SEQ ID NO 26
```

<211> LENGTH: 40
<212> TYPE: DNA
<213> ORGANISM: Artificial
<220> FEATURE:
<223> OTHER INFORMATION: Probe B40

<400> SEQUENCE: 26
agttgggtgc acgagtgggt tacatcgaac tggatctcaa        40

<210> SEQ ID NO 27
<211> LENGTH: 40
<212> TYPE: DNA
<213> ORGANISM: Artificial
<220> FEATURE:
<223> OTHER INFORMATION: Probe C40

<400> SEQUENCE: 27
tagactggat ggaggcggat aaagttgcag gaccacttct        40

<210> SEQ ID NO 28
<211> LENGTH: 60
<212> TYPE: DNA
<213> ORGANISM: Artificial
<220> FEATURE:
<223> OTHER INFORMATION: Probe A60

<400> SEQUENCE: 28
ttttatggtg cactctcagt acaatctgct ctgatgccgc atagttaagc cagccccgac        60

<210> SEQ ID NO 29
<211> LENGTH: 60
<212> TYPE: DNA
<213> ORGANISM: Artificial
<220> FEATURE:
<223> OTHER INFORMATION: Probe B60

<400> SEQUENCE: 29
gtgggttaca tcgaactgga tctcaacagc ggtaagatcc ttgagagttt tcgccccgaa        60

<210> SEQ ID NO 30
<211> LENGTH: 60
<212> TYPE: DNA
<213> ORGANISM: Artificial
<220> FEATURE:
<223> OTHER INFORMATION: Probe C60

<400> SEQUENCE: 30
cttcccggca acaattaata gactggatgg aggcggataa agttgcagga ccacttctgc        60

STABLE HYBRID

BACKGROUND OF THE INVENTION

1. Field of the Invention

The present invention relates to formation of a stable hybrid between a sample nucleic acid and a probe immobilized on a substrate. The present invention also relates to a probe for use in forming such a hybrid, a PCR primer, a probe carrier and designing methods thereof.

2. Related Background Art

As is represented by the Human Genome Project, gene sequences of various types of organisms have been elucidated and the relationships between genes and the mechanism of life activity, diseases, constitutional predispositions and so forth are investigated. It is now understood that by determining the presence or absence of a certain gene or its (expression) amount, not only the feature or type of a disease but also the effective therapy thereof may be determined.

Various methods have been proposed for detecting the presence or absence of a specific gene in a test sample and determining the expression amount of the gene, among which, the following method is applicable to a wide variety of samples. This method comprises the steps of selecting (determining) a partial nucleotide sequence specific to a target gene, and detecting the presence or absence or the expression amount of the partial sequence, thereby determining the presence or absence of the gene or its expression amount. More specifically, according to this method, a nucleic acid (probe) of which sequence is complementary to the selected partial sequence is prepared, and the probe and a test sample are hybridized to detect whether a hybrid is formed or not by certain means, whereby the presence or absence of the gene in the sample is determined.

This method of detecting a specific nucleic acid by using hybridization can be used in both solid and liquid phases. For example, hybridization in a liquid phase is performed as follows: a probe labeled with a labeling agent of which spectroscopic property changes when the probe becomes double stranded; then a test sample is added to a solution of the probe; and spectroscopic change is measured. In this way, the presence or absence of a specific nucleic acid can be determined.

On the other hand, hybridization on a solid is typically performed as follows: a probe is immobilized onto a substrate; then, a sample labeled with a detectable labeling agent is applied to the substrate; and a signal emitted from the labeling agent on the substrate is measured. Typical examples are microarrays where probes are immobilized on a flat glass or metal substrate, and beads that are fine particles having immobilized probes thereon. Solid-phase hybridization is preferably used for the following reasons: B/F separation (separation of bound form and free form) is easy; detection can be performed in a minute area and with high sensitivity; if a plurality of types of probes are discretely arranged, simultaneous detection of a plurality of items can be made; and solid substrates are easy to handle or use.

For example, U.S. Pat. No. 6,410,229 to Affymetrix Inc. (USA) discloses a method for detection and quantification of a specific nucleic acid in a sample by hybridizing a labeled nucleic acid with an oligo DNA synthesized on a flat substrate, and detecting fluorescence emitted from the hybrid. On the other hand, Japanese Patent Publication No. 2001-128683 (Fuji Photo Film Co., Ltd.) discloses detection of 22 mer ssDNA by using a DNA array prepared using a substrate to which amino groups had been introduced beforehand.

SUMMARY OF THE INVENTION

As described above, the detection method using solid-phase hybridization has an advantage over other detection methods in sensitivity. However, the sensitivity of conventional solid-phase hybridization detection methods is not enough to satisfy needs for detecting a very small amount of nucleic acid. To detect a hybrid with higher sensitivity and higher specificity, improvement in the solid-phase hybridization detection method is demanded.

To increase detection accuracy, improvement has been made from various aspects. One method for improving the detection performance is to increase binding between the probe and the target by increasing the Tm of the probe-target. Alternatively, labeling rate of the target with a labeling agent is increased, a labeling agent emitting a strong signal is used, or the labeling agent itself is labeled (multi-labeling), to increase sensitivity.

However, the method of increasing binding of a probe to a target has a problem in that nonspecific adsorption and binding take place, greatly reducing specificity of target binding. Therefore, the effect of this method is limited. On the other hand, the method of improving labeling has a problem in that the S/N ratio and quantitativeness may decrease. The effect of this method is also limited.

Another method for improving hybridization efficiency is to stabilize the hybrid formed between a probe and a target. To stabilize the hybrid, it is necessary to optimize the hybridization conditions, i.e., salt concentration and concentration of the denaturing agent. However, this method also has a problem in that specificity and S/N ratio may decrease.

In these circumstances, it has been strongly desired to develop a method of forming a stable hybrid, a probe designing method and a sample preparation method in order to detect a nucleic acid more efficiently.

The present inventors have intensively studied the aforementioned problems, and found out that a probe and a sample nucleic acid can hybridize to form a stable hybrid if a certain relationship between the probe immobilized on a substrate and the sample nucleic acid is satisfied.

The present invention provides a hybrid formed between a probe nucleic acid and a sample nucleic acid, wherein the probe nucleic acid and the sample nucleic acid are hybridized between a target sequence present in a target strand of the sample nucleic acid and a complementary probe sequence present in the probe nucleic acid, wherein the target strand of the sample nucleic acid is longer than the probe nucleic acid, and when the number of bases of a 5' portion of the target strand not being the target sequence is designated as L1, and the number of bases of a 3' portion of the target strand not being the target sequence is designated as L2, L1 and L2 satisfy the following relationship: 0 L1/L2 1.5.

The present invention also provides a probe designed so as to form the above-described hybrid with a target strand having a target sequence.

The present invention also provides a probe set comprising not less than two probes each being a probe described above.

The present invention also provides a probe carrier having probes for detecting a target nucleic acid immobilized, wherein not less than 50% of all probes is occupied by the above probe set. The present invention also provides a method of designing a probe so as to be form the above-described hybrid with a target strand having a target sequence.

The present invention also provides a PCR primer for preparing a sample nucleic acid capable of forming a hybrid that is described above with a probe that is described above.

The present invention also provides a PCR primer for preparing a sample nucleic acid capable of forming an above-described hybrid with an above-described probe.

The present invention also provides a method of detecting a sample nucleic acid by detecting a hybrid obtained by reacting a sample nucleic acid with a probe nucleic acid immobilized in a substrate, the sample nucleic acid being longer than the probe nucleic acid, wherein the sequence of the probe nucleic acid is designed so as to form a hybrid satisfying features (1) and (2):
(1) the hybrid is formed between a target sequence present in a target strand of the sample nucleic acid and a complementary probe sequence present in the probe nucleic acid; and
(2) the target strand of the sample nucleic acid is longer than the probe nucleic acid, and when the number of bases of a 5' portion of the target strand not being the target sequence is designated as L1, and the number of bases of a 3' portion of the target strand not being the target sequence is designated as L2, L1 and L2 satisfy the following relationship:

$$0 \leq L1/L2 \leq 1.5$$

When the sample nucleic acid is a product amplified by PCR using a sample nucleic acid, it is desirable that the PCR primer herein and the probe are designed such that they can form a hybrid satisfying the features (1) and (2).

The present invention also provides a kit for detecting a sample nucleic acid comprising
 a PCR primer for amplifying a sample nucleic acid having a target strand having a target sequence, from the test-sample nucleic acid, and
 a probe nucleic acid immobilized onto a substrate and prepared for determining the presence and absence of the target sequence in an amplified product which is amplified using the PCR primer and the test-sample nucleic acid as a template;
 wherein the sequences of the primer and the probe nucleic acid are designed so as to form a hybrid satisfying features (1) and (2):
(1) the hybrid is formed between a target sequence present in a target strand of the sample nucleic acid and a complementary probe sequence present in the probe nucleic acid; and
(2) the target strand of the sample nucleic acid is longer than the probe nucleic acid, and when the number of bases of a 5' portion of the target strand not being the target sequence is designated as L1, and the number of bases of a 3' portion of the target strand not being the target sequence is designated as L2, L1 and L2 satisfy the following relationship:

$$0 \leq L1/L2 \leq 1.5.$$

A hybrid according to the present invention may be formed of any combination of a probe nucleic acid and a sample nucleic acid as long as the probe nucleic acid is immobilized onto a substrate. A preferable example of the present invention is a hybrid formed by immobilizing an oligonucleotide or DNA such as cDNA on a flat substrate as a probe, e.g., DNA microarray, and hybridizing a sample nucleic acid labeled with a detectable marker with the probe.

A probe may be immobilized onto a substrate by various methods, such as covalent bond, ionic bond and adsorption. A hybrid of the present invention can be formed no matter which immobilization method is employed.

Of these immobilization methods, covalent bond is preferable in view of forming a stable hybrid because it relatively not influenced by various conditional changes associated with hybridization such as heating and high salt concentration. As covalent bond, any type of bonding is applicable without limitation as long as bonding is made between a functional group capable of being introduced into a substrate and a functional group capable of being introduced into a nucleic acid probe. When a synthetic oligonucleotide is used as a probe, a thiol group, amino group, or a derivative thereof is frequently used as a functional group for use in modification since they can easily introduced. Of various methods, a method of introducing the functional group as mentioned above into the 5' end and the 3' end of an oligonucleotide is convenient in view of a synthetic process. A probe, which is immobilized on a substrate via such a functional group introduced to one end of an oligonucleotide, can be preferable used to form a hybrid according to the present invention.

In addition to the functional groups introduced to the 5' end or the 3' end, a functional group introduced into the middle portion of an oligonucleotide sequence, or a functional group of an artificial nucleotide derivative introduced into a sample nucleic acid during synthesis may be used for immobilization.

Since a nucleic acid has negative charge as a whole owing to the phosphate ester bonds in the skeleton of a nucleic acid, it can be adsorbed to a positively charged coating material introduced onto a substrate or to the substrate itself.

A probe to be immobilized onto a substrate may differ in chain length. The specificity and binding force of a probe varies depending upon chain length of the probe. Oligonucleotides of 15 to 30 mers, 31 to 50 mers and 51 to 80 mers are frequently used as a probe to be immobilized onto a substrate. They are also suitable for a hybrid according to the present invention.

Although nucleic acid such as oligonucleotide is generally used as a probe, a peptide nucleic acid (PNA), to which strong hybridization can be expected, may be used. In that case, more stable hybrids can be obtained, by satisfying the relationship between L1 and L2 according to the present invention.

More specifically, as long as the value of L1/L2 falls within the range of 0 to 1.5, a stable hybrid according to the present invention can be formed. A more stable hybrid can be formed in particular, when the value of L1/L2 falls within the range of 0 to 1.

The sample nucleic acid herein means nucleic acid having a target sequence that hybridizes with a probe and subjected to a reaction with the probe. It may be the test sample itself, or a nucleic acid fragment taken out from the sample by any means. The target sequence is not particularly limited, as long as it can specify a sequence that the test sample is presumed to contain. Depending upon the type of sample nucleic acid, the target sequence may be a part or whole of the sample nucleic acid to be detected in a test sample, or a complementary sequence thereof. The sample nucleic acid has a target strand containing the target sequence (complementary to a probe sequence) to be hybridized with a probe. Any type of nucleic acid, for example, double stranded DNA, single stranded DNA, and RNA, may be applied to the present invention, as long as it can hybridize with a probe immobilized onto a substrate under appropriate conditions. When the sample nucleic acid is a single strand DNA, the DNA itself is a target strand.

A method of preparing a sample nucleic acid is not particularly limited and a PCR amplification method and reverse transcription method of RNA are often used. A PCR product and reverse transcription product obtained by these methods may be preferably used in order to form a hybrid of the present invention.

When solid-phase hybridization is used for detecting a specific base sequence, as is in the case of a DNA microarray, sample nucleic acid is usually labeled by binding a labeling agent. A sample nucleic acid in which a labeling agent is incorporated is also preferably applied to the present invention for forming a hybrid.

As a labeling agent, a fluorescent substance is generally used since it is easy to handle and detectable with high sensitivity. Also, a radioisotope can be preferably used as a marker since it has excellent sensitivity. Although there are great many choices for fluorescent substances, any one of fluorescent substances may be used. Of them, fluorescent dyes such as Cy3 and Cy5 are widely used and can be preferably used in a hybrid according to the present invention.

The length of a sample nucleic acid is not particularly limited and any length of a nucleic acid may be used to form a hybrid. Of them, a sample nucleic acid having a chain length of not less than 500 bp is preferable since a stable hybrid can be formed. A more stable hybrid may be formed if the chain length of a sample nucleic acid falls within the range of 500 bp to 2500 bp.

A designed probe is also provided in the present invention in order to hybridize with a sample nucleic acid to form the hybrid mentioned above. More specifically, the present invention provides a probe that is designed by setting a probe-capturing region in a sample nucleic acid at a position at which a hybrid according to the present invention can be formed, thereby forming a hybrid satisfying the positional relationship between a solid-phase probe and a sample nucleic acid.

The present invention also provides a probe set having not less than two different types of probes. To provide such probes, it is necessary to design the sequence of a probe. Therefore, a method of designing a probe is also provided.

In order to use a probe efficiently for detecting a target nucleic acid (target sequence), the probe is immobilized onto a solid carrier to facilitate B/F separation. Therefore, the present invention provides a probe carrier having at least one probe is immobilized on a solid carrier. As an example of such a carrier, a DNA microarray may be mentioned. Such a DNA microarray is one of preferable examples for a probe immobilized carrier according to the present invention.

As a sample nucleic acid, a PCR product may be often used as mentioned above. To prepare a PCR product, a PCR primer is used. Therefore, the present invention provides a PCR primer designed so as to satisfy the conditions of L1 and L2.

According to the present invention, it is possible to form a stable hybrid between a probe immobilized onto a substrate and a sample nucleic acid, and obtain the conditions in which the hybrid is formed. Furthermore, it is possible to provide a probe and a primer satisfying the conditions of the present invention, and further provide a method of designing such a probe and a primer, and a probe carrier on which such a hybrid is formed. According to the present invention, a nucleic acid can be detected efficiently with high sensitivity by a method of detecting a nucleic acid by use of hybridization performed on a substrate.

Other features and advantages of the present invention will be apparent from the following description taken in conjunction with the accompanying drawings, in which the same reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

A hybrid according to the present invention will be explained in more detail.

A hybrid provided by the present invention is formed between a probe and a sample nucleic acid having a complementary sequence to the probe in part and satisfies the following relationship:

$$0 \leq L1/L2 \leq 1.5$$

wherein the chain length (base number) of 5' portion upstream the target sequence of the sample nucleic acid is designated as L1, and that of 3' portion downstream the target sequence as L2.

Figure 1:
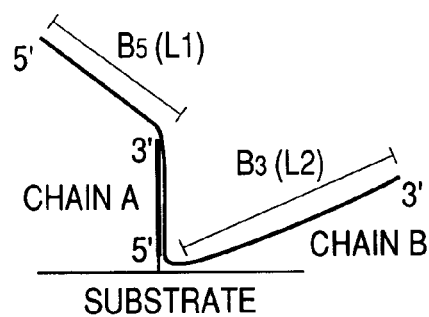
FIG. 1 shows an illustration of a hybrid between a probe (Strand A) immobilized on a substrate and a sample nucleic acid (Strand B) in which the length of 5' portion upstream the hybridized region of the sample nucleic acid is designated as $B_5$, and the length of 3' portion downstream the hybridized region as $B_3$.

FIG. 1 shows a schematic view of an example hybrid of the present invention between a single stranded probe (Chain A) immobilized on a substrate at the 5' end and a single stranded nucleic acid (Chain B) having a complementary sequence to the Chain A. In this figure, the chain length of 5' portion upstream the target sequence of the chain B designated as $B_5$(L1), and that of 3' portion downstream the target sequence designated as $B_3$(L2) satisfy the following relationship:

$$B_5 \leq B_3.$$

If the value of L1/L2 ranges from 0 to 1.5, a stable hybrid of the present invention can be formed. To obtain more stable hybrid, it is desirable to set an L1/L2 value within the range of from 0 to 1.

It is possible to form a hybrid of the present invention as long as a probe is immobilized on a substrate or a solid-phase surface no matter how the probe is immobilized. A DNA microarray having a nucleic acid immobilized on a glass substrate is a representative example. Various types of DNA microarrays are applicable to forming a hybrid of the present invention. A material for a substrate includes a resin, metal, metal film, and fiber other than glass. As to form of a substrate, any form may be used including fine particles, a tip of an optical fiber, porous material, and fiber.

Any binding means such as adsorption and chemical bond may be used to immobilize a probe for hybrid formation. For example, ionic bond is mentioned in the section "SUMMARY OF THE INVENTION". If a glass substrate or a resin surface is coated to have amino groups in advance, unmodified nucleic acid can be immobilized by ionic bond on the substrate or resin surface by only applying it thereto.

Alternatively, if a modified oligonucleotide having a functional group, such as a thiol group or amino group, introduced to the 5' end, 3' end or the middle portion of a nucleic acid, the nucleic acid can be immobilized on a substrate through a reaction of the introduced functional group. For example, in case of amino group, a succinimide group, which efficiently reacts with the amino group, is introduced to the solid-phase surface in advance, and an oligonucleotide is modified with the amino group at the 5' end, 3' end, etc., whereby covalent bond is easily formed between the oligonucleotide and the solid-phase surface simply by applying the oligonucleotide thereto. The oligonucleotide thus bound on the solid-phase surface can be suitably used as a probe for forming a hybrid of the present invention.

When a thiol group is used, similarly maleimide group is introduced to the substrate, an oligonucleotide having thiol group can be easily covalently bonded to the substrate. The oligonucleotide thus bound on the substrate can be suitably used as a probe for forming a hybrid of the present invention.

Besides DNA, PNA can be used as a probe. Also cDNA may be used as a probe. However, in order to form a hybrid more accurately, a chemically synthesized oligonucleotide is frequently used as a probe. Such a probe desirably has a base chain length of 15 to 30 mers, 31 to 50 mers, or 51 to 80 mers, to be used appropriately according to their characteristics.

A sample nucleic acid for use in forming a hybrid of the present invention is not particularly limited and may be used as long as it is longer than a probe (immobilized on a substrate) in terms of chain length.

A hybrid of the present invention is suitable for detecting a nucleic acid sequence on a DNA microarray or beads. In this case, as a sample nucleic acid, a PCR amplification product, a transcription product, reverse transcription product, and so forth are usually used. These nucleic acids are preferably used to form a hybrid of the present invention. To explain more specifically, a sample nucleic acid may be either double stranded or single stranded and either DNA or RNA to form a hybrid of the present invention.

Furthermore, when formation of a hybrid is detected by a spectroscopic means, a sample nucleic acid must be labeled with a labeling agent such as a fluorescent substance. A hybrid of the present invention can be formed even if a nucleic acid labeled with such a labeling agent is used. Of the fluorescent labeling agents, Cy dyes including Cy3 and Cy5 (manufactured by Amersham Biosciences) are frequently used. A sample nucleic acid including a fluorescent substance is applicable to form a hybrid of the present invention without any problem.

As a labeling agent having the same detection sensitivity as a fluorescent substance, $^{32}P$ radioisotope is often used. In this case, a hybrid of the present invention can be sufficiently formed.

A hybrid of the present invention can be formed regardless of the chain length of the sample nucleic acid. When the length of a sample nucleic acid is 500 bp or more, more stable hybrid can be formed. When the length of a sample nucleic acid is from 500 bp to 2500 bp, further more stable hybrid can be formed.

When a sample nucleic acid is, for example, a double stranded DNA, a sample nucleic acid may be double stranded with its complementary strand except for the hybridized region. Even in this case, a hybrid of the present invention can be formed. More specifically, if there are portions satisfying the aforementioned relationship of L1 and L2 in the hybrid formed between the immobilized probe on a substrate and the sample nucleic acid, the hybrid is a highly stable hybrid according to the present invention.

In the case where the double stranded portion formed between a probe and a sample nucleic acid is shorter than the length of the probe, that is, the probe containing a mismatch region is hybridizing with a sample nucleic acid, a stable hybrid can be formed. In this case, provided that the length of a sample nucleic acid between the 5' end to the end of a double stranded portion is represented by L1 and the length of the sample nucleic acid between the 3' end to the other end of the double stranded portion is represented by L2, if L1 and L2 satisfy the aforementioned relationship between L1 and L2, a hybrid of the present invention can be formed.

Usually, probes for detecting the presence or absence of a target nucleic acid based on a specific hybrid formation between the probe immobilized on a substrate and a target are designed so as to detect the sample nucleic acid specifically with high sensitivity. Since most of such probe designing methods consider only the base sequence, effective probes for liquid-phase hybridization can be designed, but design of probes for solid-phase hybridization is not always satisfactory. Therefore, the hybrid formation conditions of the present invention give an indication to the stability of a hybrid on a substrate. Accordingly, the present invention also provides a method of designing a probe on a solid substrate that gives stable hybrid of the present invention.

The present invention further provides a probe designed in accordance with this probe designing method. Moreover, the present invention provides a set of probes containing a plurality of (two or more) probes.

A DNA microarray is an example of a probe carrier in which a plurality of different sequence of probes are immobilized on a solid carrier. When a probe of the present invention is used as probes constituting such a probe carrier, not less than 50% of all probes on the carrier is preferably occupied by probes according to the present invention, and not less than 70% is more preferable. Such a probe carrier having a plurality of probes (probe set) immobilized on a carrier is also provided by the present invention.

The probes satisfying the conditions of the present invention are preferably present in a ratio of 50% or more, and more preferably, in a ratio of 75% or more to the entire number of probes of a probe carrier.

When a PCR product is used as a sample nucleic acid, the relative position of the region corresponding to the probe (probe region) in the sample nucleic acid may vary depending upon the design of primers for PCR amplification. It is ideal that the probe region of a sample nucleic acid is designed so as to satisfy the aforementioned conditions (represented by the equation). Sometimes a probe region does not meet the conditions, for example, in view of specificity. In such a case, first a probe region is designed and then a primer for a sample nucleic acid may be designed such that the probe region satisfies the condition of the present invention. Therefore, the present invention also provides a primer for amplifying a sample nucleic acid having a predetermined probe region to form a hybrid satisfying the aforementioned conditions.

EXAMPLES

The present invention will be described in detail below by way of Examples. Examples described below are preferred embodiments according to the present invention and will not limit a technical scope of the present invention.

Example 1

I. PCR for pUC118 EcoRI/BAP (1) Primer Design

As a model sample having a target sequence, a commercially available vector, pUC118 EcoRI/BAP of 3162 bp (manufactured by Takara) was chosen. Three primers having the following sequences were designed for the vector. The base-sequence data of full-length pUC118 EcoRI/BAP was given by Takara and also available from a database known to the public.

Primers were designed in consideration of base sequence, GC % and melting temperature (Tm) so as to specifically and efficiently amplify a desired portion of pUC118 EcoRI/BAP by PCR amplification.

Three primers: two forward primers (F1, F2) and one reverse primer (R1), were designed. When PCR amplification was performed by using pUC118 EcoRI/BAP as a template, and a set of primers, that is, a combination of F1 and R1 or F2 and R1, a PCR product of 1324 bp (PCR product 1) and a PCR product of 940 bp (PCR product 2) were obtained. The base sequence of each primer designed herein and the melting temperature (Tm) of corresponding hybrid are shown in Table 1.

TABLE 1

| Name | Base sequence | Tm (° C.) |
|---|---|---|
| F1 | 5' TGATTTGGGTGATGGTTCACGTAG 3' (SEQ ID NO:1) | 60.9 |
| F2 | 5' GAGCTGCATGTGTCAGAGGTTT 3' (SEQ ID NO:2) | 61.0 |
| R1 | 5' ATCAGCAATAAACCAGCCAGCC 3' (SEQ ID NO:3) | 61.5 |

Figure 2:
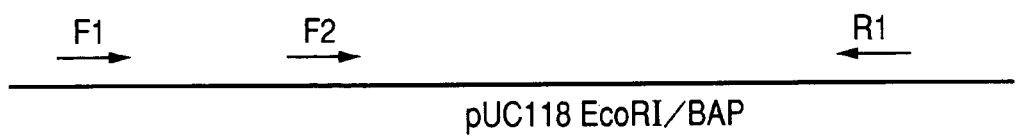
FIG. 2 shows the positions of three primers to pUC118 EcoRI/BAP in which the arrow of each primer is directed from the 5' to 3'.

The positional relationship between three primers and the full-length pUC118 EcoRI/BAP are shown in FIG. 2. The arrow of each primer is directed from the 5' to 3'.

(2) Synthesis of Primer

Three primers designed in Example 1 (1) were synthesized. Each primer was synthesized by a DNA synthesizer in accordance with a conventional method so as to have the designed base sequence. The DNA strands thus obtained were purified by cartridge purification to obtain three primers, each of which was diluted with a TE buffer to 10 µM.

(3) PCR Amplification Reaction

A PCR amplification reaction was performed by using three primer synthesized in Example 1 (2), a vector, pUC118 EcoRI/BAP (manufactured by Takara), as a template DNA, and a PCR kit, HotStarTaq Master Mix (manufactured by QIAGEN). To the MasterMix containing 4 types of deoxynucleotides, DATP, dCTP, dTTP and dGTP, Cy3dUTP (manufactured by Amersham Biosciences) was added to fluorescent label the PCR product.

PCR amplification was performed by using two sets of a forward primer and a reverse primer combinations described in Example 1 (1). PCR was performed in accordance with the conditions shown in the protocol below. PCR solutions (1) and (2) were prepared in accordance with the recipe shown in Table 2 below.

TABLE 2

| Composition of reaction solution | |
|---|---|
| Component | Content |
| Master Mix (manufactured by QIAGEN) | 25 µl |
| Template DNA (diluted pUC118, Manufactured by Takara) | 1 µl (10 ng) |
| Forward Primer F1 (Solution 1) or Forward Primer F2 (solution 2) | 2.5 µl (25 pmol/tube) |
| Reverse Primer(R1) | 2.5 µl (25 pmol/tube) |
| Cy3 dUTP(1 mM, manufactured by Amersham Biosciences) | 2 µl (25 pmol/tube) |
| H₂O | 17 µl |
| Total | 50 µl |

Each reaction solution prepared above was subjected to a PCR amplification reaction using a commercially available thermal cycler and in accordance with the temperature cycle protocol shown in Table 3 below. To explain more specifically, the reaction solution was held at 95° C. for 15 minutes, subjected to denaturation at 92° C. for 45 seconds, annealing at 55° C. for 45 seconds, and extention at 72° C. for 45 seconds. This cycle was repeated 25 times. Finally, the reaction solution was allowed to stand at 72° C. for 10 minutes.

TABLE 3

| Temperature conditions for PCR amplification reaction | | | | |
|---|---|---|---|---|
| Step | Temperature | | Holding time | Repetition |
| 1 | 95° C. | | 15 min. | |
| 2 | 92° C. | (denaturation) | 45 sec. | 25 cycles |
| 3 | 55° C. | (annealing) | 45 sec. | |
| 4 | 72° C. | (elongation) | 1 min. | |
| 4 | 72° C. | | 10 min. | |

After completion of the PCR, an amplified product was purified by use of a purification column (Qiagen QIAquick PCR Purification Kit). After the purification, the volume of a solution containing the PCR amplification product was adjusted to 50 µl. The PCR amplification product solution was purified, an aliquot was taken therefrom, and then, electrophoretically analyzed in accordance with a conventional method. Presence of a band of desired base chain length was confirmed in each of the PCR products (1) and (2).

II. Preparation of DNA Microarray (1) Design and Synthesis of Probe

Three types of probes were designed for the PCR product 1 obtained above. Each of the probes was designed in the same manner as with primer design so as to specifically recognize a certain base sequence (target sequence) in the sample (PCR product 1) and to have the similar GC % and hybrid melting temperature (Tm).

The base sequences and Tm values of designed probes are shown in Table 4.

TABLE 4

| Name | Base sequence | Tm (° C.) |
|---|---|---|
| P1 | 5' ATGGTGCACTCTCAGTACAATCTGC 3' SEQ ID NO:4 | 75.7 |

TABLE 4-continued

| Name | Base sequence | Tm (° C.) |
|---|---|---|
| P2 | 5' GTGGGTTACATCGAACTGGATCTCA 3'<br>SEQ ID NO:5 | 75.8 |
| P3 | 5' GATAAAGTTGCAGGACCACTTCTGC 3'<br>SEQ ID NO:6 | 75.7 |

In this probe design, the DNA strand that hybridizes with the probe was a strand extending from R1 primer.

Probes P2 and P3 can also form hybrids with the PCR product 2.

In the hybrids between PCR products 1 and 2 and the corresponding probes, the length of the 5' portion of the target strand upstream the hybrid region is represented by L1 and that of 3' portion downstream of the hybrid region is represented by L2. The values of L1, L2 and L1/L2 with respect to each of the PCR products are shown in Table 5.

TABLE 5

| PCR product | Probe | L1 | L2 | L1/L2 |
|---|---|---|---|---|
| 1 | P1 | 1053 | 246 | 4.28 |
| F1-R1 | P2 | 545 | 754 | 0.72 |
|  | P3 | 35 | 1264 | 0.03 |
| 2 | P2 | 545 | 370 | 1.47 |
| F2-R1 | P3 | 35 | 880 | 0.04 |

Figure 3:
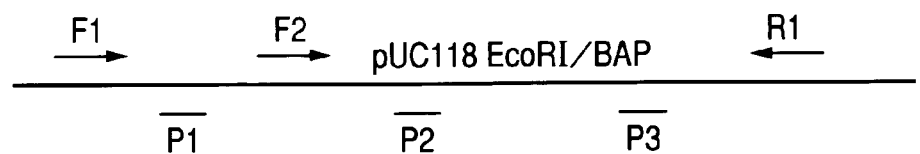
FIG. 3 shows three primers and three probes to pUC118 EcoRI/BAP.

The positional relationship between three types of probes, three primers and full-length pUC118 EcoRI/BAP is shown in FIG. 3.

(2) Cleaning of Glass Substrate

A glass substrate made of synthetic quartz of 25 mm width×75 mm length×1 mm thickness (manufactured by Iiyama Tokushu Glass) was placed in a heat and alkali resistant rack and soaked in an ultrasonic washing solution prepared at a predetermined concentration. After the substrate was allowed to stand overnight in the washing solution, it was subjected to ultrasonic washing for 20 minutes. Thereafter, the glass substrate was taken out and lightly rinsed with pure water and then ultrasonically washed in ultrapure water for 20 minutes. The glass substrate was then soaked in 1N aqueous sodium hydroxide solution heated to 80° C. for 10 minutes and subjected again to pure water washing and ultrapure water washing steps. In this manner, a clean quart glass substrate for use in a DNA microarray was prepared.

(3) Surface Treatment

A silane coupling agent, KBM-603 (manufactured by Shin-Etsu Silicone) was dissolved in pure water to a concentration of 1%. The resultant solution was stirred at room temperature for 2 hours. Subsequently, the clean quartz substrate was soaked in the aqueous solution of the silane coupling agent and allowed to stand for 20 minutes at room temperature. The glass substrate was taken out, lightly washed with pure water, and dried by blowing with nitrogen gas to both surfaces of the substrate. The glass substrate dried with nitrogen gas was baked in an oven at 120° C. for one hour to complete the treatment with the coupling agent. In this manner, an amino group derived from silane coupling agent was introduced into the surfaces of the glass substrate.

While, N-(6-maleimidocaproyloxy)succinimide (hereinafter simply referred to as "EMCS") manufactured by Doujin Kagaku Kenkyusho was dissolved in a solvent mixture containing dimethylsulfoxide and ethanol in a ratio of 1:1 to a final concentration of 0.3 mg/ml to prepare an EMCS solution. After baking, the treated glass substrate was allowed to cool and soaked in the EMCS solution prepared above at room temperature for 2 hours. During the soaking step, the amino group introduced into the glass substrate was allowed to react with a succinimide group derived from EMCS, thereby introducing a maleimide group derived from EMCS to the surfaces of the glass substrate. The glass substrate was taken out from the EMCS solution, washed with a solvent mixture of dimethylsulfoxide and ethanol mentioned above, washed further with ethanol and allowed to dry in a nitrogen gas atmosphere.

(4) Synthesis of Probe DNA

Three types of probes designed in Step (1) above were synthesized.

To covalently bond a probe DNA to the glass substrate having a maleimide group introduced into the surface thereof, the 5' end of the probe DNA was modified with a thiol group in accordance with a conventional method. Thereafter, the protecting group that had been introduced to prevent side reactions during DNA synthesis was removed and HPLC purification and desalination treatment were performed.

The obtained probe DNA was dissolved in pure water and aliquots were subjected to lyophilization to remove water.

(5) Ejection of Probe DNA by BJ Printer and Binding to Substrate Surface

An aqueous solution was prepared containing 7.5% by weight of glycerin, 7.5% by weight of thiodiglycol, 7.5% by weight of urea, and 1.0% by weight of acetylenol EH (manufactured by Kawaken Fine Chemicals Co., Ltd.). Subsequently, an aliquot of the probe DNA prepared above was dissolved in the solvent mixture prepared above to a final concentration of 10 μM. The resultant probe DNA solution was loaded in an ink tank of a bubble-jet printer, BJF-850 (trade name, manufactured by Canon Inc.), and the tank was installed in a print head.

Note that the bubble-jet printer was modified so as to print on a flat plate. The modified bubble-jet printer can spot liquid drops of a DNA solution (about 5 pl per drop) at about 120 μm pitch by inputting a printing pattern according to a predetermined file preparation method.

Using the modified bubble-jet printer, a probe DNA solution was spotted on a glass-substrate surface. A print pattern was previously designed so as to spot 16 spots for each probe on one DNA microarray and inkjet printing was performed. After spotting of the probe DNA solution onto a substrate in a desired pattern was confirmed by a magnifier, the microarray was left alone in a humidified chamber at normal temperature for 30 minutes to allow a maleimide group on the surface of a glass substrate to react with a thiol group at the 5' end of probe DNA.

(6) Washing

After the reaction was performed for 30 minutes in the humidified chamber, probe DNA remaining unreacted on the glass-substrate surface was washed out by a 10 mM phosphate buffer (pH 7.0) containing 100 mM NaCl. In this way, a DNA microarray was obtained which had 16 spots of predetermined single-stranded probe DNA immobilized on the glass-substrate surface.

III. Hybridization Reaction

Hybridization was performed by use of two types of PCR amplification products prepared as a sample nucleic acid in Step I on the DNA microarray prepared in Step II.

(1) Blocking of DNA Microarray

Bovine serum albumin (BSA, fraction V, manufactured by Sigma) was dissolved in a 10 mM phosphate buffer containing 100 mM NaCl to make a concentration of 1% by weight.

To this solution, the DNA microarray prepared in Step II was soaked at room temperature for 2 hours to block the glass-substrate surface. After completion of the blocking, the substrate was washed with 2×SSC solution [(300 mM of NaCl, 30 mM of sodium citrate (trisodium citrate dehydrate $C_6H_5Na_3.2H_2O$), pH 7.0)] containing 0.1% by weight sodium dodecyl sulfate (SDS) and then rinsed with pure water. Thereafter, the DNA microarray was dewatered by a spin dryer.

(2) Preparation of Hybridization Solution

PCR products were prepared so as to have the same molar concentration. Hybridization solutions were prepared by using the PCR amplification product solutions so as to obtain final concentrations mentioned below.

<Hybridization Solution>

6×SSPE/10% formamide/PCR amplification product solution (6×SSPE contains 900 mM NaCl, 60 mM $NaH_2PO_4H_2O$, and 6 mM EDTA, pH 7.4).

(3) Hybridization

The microarray dewatered was placed in a hybridization apparatus (Hybridization Station, manufactured by Genomic Solutions Inc.) and hybridization was performed using the hybridization solution of the aforementioned composition in accordance with the conditions and procedure described below.

<Conditions and Procedure of Hybridization>

The hybridization solution was heated to 6.5° C. and allowed to stand for 3 minutes, subsequently at 92° C. for 2 minutes, and then at 55° C. for 4 hours. Thereafter, the DNA microarray was washed with 2×SSC, 0.1% SDS at 25° C., further with 2×SSC at 20° C., and if necessary, rinsed with pure water in accordance with a conventional manual, and finally dewatered by a spin drier to dry.

TABLE 6

| Operation | Operation procedure/conditions |
|---|---|
| Reaction | 65° C. 3 min → 92° C. 2 min → 55° C. 4 h |
| Wash | 2 × SSC/0.1% SDS at 25° C. |
|  | 2 × SSC at 20° C. |
| (Rinse) | $H_2O$ (manual rinsing) |
| Dry | Spin dry |

(4) Fluorescence Measurement

After completion of the hybridization reaction, the DNA microarray spin-dried was subjected to fluorescence measurement using a DNA-microarray fluorescence detection device (Genepix 4000B, manufactured by Axon Instruments) to measure fluorescence emitted from a hybrid. The fluorescent intensity values of PCR amplification products 1 and 2 measured with respect to individual probes are shown in Table 7 below.

In computation of fluorescent intensity, the fluorescent intensity of the portion where no DNA-probe spot was present was subtracted as a background value from the apparent fluorescent intensity of each DNA-probe spot. Measurement is performed twice and an average value thereof is shown.

TABLE 7

| PCR product | Probe | Fluorescent intensity | L1/L2 |
|---|---|---|---|
| 1 | P1 | 10 | 4.28 |
| F1-R1 | P2 | 4607 | 0.72 |
|  | P3 | 7369 | 0.03 |

TABLE 7-continued

| PCR product | Probe | Fluorescent intensity | L1/L2 |
|---|---|---|---|
| 2 | P2 | 725 | 1.47 |
| F2-R1 | P3 | 1504 | 0.04 |

From the results above, with probes designed to have virtually the same Tm value with respect to the same sample nucleic acid, the fluorescent intensity greatly differs with the probes. This fact suggests that the stability of hybrids greatly differs. High fluorescent value means that many hybrids are formed, in other words, hybrids are stably formed. The stability of a hybrid varies depending upon the ratio of L1/L2 (L1 is the length of 5' portion upstream the hybrid portion of the target, and L2 is the length of 3' portion downstream the hybridized portion of the target stand of the sample). It was found out that a hybrid was more stable when L1 is shorter than L2.

Example 2

I. PCR for pUC118 EcoRI/BAP (1) Primer Design

As a model sample having a target sequence, a commercially available vector, pUC118 EcoRI/BAP of 3162 bp (manufactured by Takara) was chosen. Primers having the following sequences were designed for the vector. The base-sequence data of full-length pUC118 EcoRI/BAP was given by Takara and also available from a database known to the public.

Primers were designed in consideration of base sequence, GC % and melting temperature (Tm) so as to specifically and efficiently amplify desired portions of pUC118 EcoRI/BAP by PCR amplification.

Fifteen types of primers including 8 forward primers (F1, F2) and 7 reverse (R1) primers were designed. PCR amplification was performed using various combination of forward primers and reverse primers and pUC118 EcoRI/BAP as a template. In this manner, when PCR amplification was performed with respect to all combinations of 8 forward primers and 7 reverse primers, various PCR products having a length ranging from 104 bp to 2345 bp were produced.

The base sequences of primers thus designed are shown in Table 8.

TABLE 8

| Name | Sequence (5' → 3') |
|---|---|
| FP1 | CTTAATCGCCTTGCAGCACATC<br>SEQ ID NO: 7 |
| FP2 | TGATTTGGGTGATGGTTCACGTAG<br>SEQ ID NO: 8 |
| FP3 | GAGCTGCATGTGTCAGAGGTTT<br>SEQ ID NO: 9 |
| FP4 | TTCTTAGACGTCAGGTGGCACT<br>SEQ ID NO: 10 |
| FP5 | CCTTCCTGTTTTTGCTCACCCA<br>SEQ ID NO: 11 |
| FP6 | GCATCTTACGGATGGCATGACA<br>SEQ ID NO: 12 |

TABLE 8-continued

| Name | Sequence (5' → 3') |
|---|---|
| FP7 | TGAAGCCATACCAAACGACGAG<br>SEQ ID NO: 13 |
| FP8 | TTACTCTAGCTTCCCGGCAACA<br>SEQ ID NO: 14 |
| RP1 | TTCGGTGATGACGGTGAAAACC<br>SEQ ID NO: 15 |
| RP2 | ACTGGTGAGTACTCAACCAAGTCA<br>SEQ ID NO: 16 |
| RP3 | ATCAGCAATAAACCAGCCAGCC<br>SEQ ID NO: 17 |
| RP4 | TACGGGAGGGCTTACCATCTG<br>SEQ ID NO: 18 |
| RP5 | CATCCATAGTTGCCTGACTCCC<br>SEQ ID NO: 19 |
| RP6 | ACGCTCAGTGGAACGAAAACTC<br>SEQ ID NO: 20 |
| RP7 | GCGCCTTATCCGGTAACTATCG<br>SEQ ID NO: 21 |

Figure 4:
FIG. 4 shows the positional relationship between 15 types of primers including forward primers F1 to F8 and reverse primers R1 to R7 to pUC118 EcoRI/BAP, in which the arrow of each primer is directed from the 5' to 3'.

Schematic positional-relationship between 15 types of primers and pUC118 EcoRI/BAP are shown in FIG. 4. The arrow on each primer indicates direction of 5' to 3'.

(2) Synthesis of Primer

Fifteen primers designed in Example 2 (1) were synthesized. Each primer was synthesized by a DNA synthesizer in accordance with a conventional method so as to have the designed base sequence. The DNA strands thus obtained were purified by cartridge purification to obtain three primers, each of which was diluted with a TE buffer to 10 μM.

(3) PCR Amplification Reaction

PCR amplification reaction was performed by using 15 types of primers synthesized in Example 2 (2), a vector, pUC118 EcoRI/BAP (manufactured by Takara), as a template DNA, and a PCR kit, AccuPrime Taq DNA Polymerase System (manufactured by Invitrogen). To a buffer in the AccuPrime kit containing 4 types of deoxynucleotides, dATP, dCTP, dTTP and dGTP, Cy3dUTP (manufactured by Amersham Biosciences) was added to fluorescent label the PCR product.

PCR amplification was performed with respect to 24 combinations of forward primers and reverse primers as shown in Table 9.

TABLE 9

| No. | Forward primer | Reverse primer | Length of PCR product |
|---|---|---|---|
| 1 | FP1 | RP1 | 811 |
| 2 | FP1 | RP2 | 1336 |
| 3 | FP1 | RP4 | 1786 |
| 4 | FP1 | RP6 | 2019 |
| 5 | FP1 | RP7 | 2345 |
| 6 | FP2 | RP4 | 1398 |
| 7 | FP2 | RP7 | 1957 |
| 8 | FP3 | RP4 | 1014 |
| 9 | FP3 | RP6 | 1247 |
| 10 | FP3 | RP7 | 1573 |
| 11 | FP4 | RP4 | 909 |
| 12 | FP5 | RP3 | 640 |
| 13 | FP5 | RP4 | 714 |
| 14 | FP6 | RP3 | 367 |

TABLE 9-continued

| No. | Forward primer | Reverse primer | Length of PCR product |
|---|---|---|---|
| 15 | FP6 | RP4 | 441 |
| 16 | FP6 | RP7 | 1000 |
| 17 | FP7 | RP3 | 190 |
| 18 | FP7 | RP4 | 264 |
| 19 | FP7 | RP5 | 305 |
| 20 | FP7 | RP6 | 497 |
| 21 | FP8 | RP3 | 104 |
| 22 | FP8 | RP4 | 178 |
| 23 | FP8 | RP5 | 219 |
| 24 | FP8 | RP6 | 411 |

The reaction conditions are as shown in the protocol below. PCR solutions were prepared in accordance with the recipe shown in Table 10 below.

TABLE 10

| Component | Content |
|---|---|
| AccuPrime Taq DNA Polumerase | 0.5 μl |
| Template DNA (diluted pUC118, Manufactured by Takara) (100 pg/μl) | 0.5 μl (50 pg) |
| Forward primer (10 μM) | 1.25 μl |
| Reverse primer (10 μM) | 1.25 μl |
| Cy3 dUTP(1 mM, manufactured by Amersham Biosciences) | 0.5 μl |
| 10 × AccuPrime PCR Buffer I | 2.5 μl |
| H$_2$O | 18.5 μl |
| Total | 25 μl |

The reaction solution prepared above was subjected to a PCR amplification reaction using a commercially available thermal cycler in accordance with the temperature cycle protocol shown in Table 11. More specifically, the reaction solution was held at 94° C. for 2 minutes, subjected to denaturation at 92° C. for 30 seconds, annealing at 55° C. for 45 seconds, and extention at 72° C. for 60 seconds. This cycle was repeated 30 times. Finally, the reaction solution was allowed to stand at 72° C. for 10 minutes.

TABLE 11

| Step | Temperature | | Holding time | Number of repeats |
|---|---|---|---|---|
| 1 | 94° C. | | 2 minutes | |
| 2 | 92° C. | Denaturation | 30 seconds | 30 cycles |
| 3 | 55° C. | Annealing | 45 seconds | |
| 4 | 72° C. | Extention | 1 minute | |
| 4 | 72° C. | | 10 minutes | |

After completion of the reaction, a PCR amplification product was purified by use of a purification column (Qiagen QIAquick PCR Purification Kit). After the purification, the volume of a solution containing the PCR amplification product was adjusted to 50 μl. The PCR amplification product solution was purified, an aliquot was taken therefrom, and then, electrophoretically analyzed in accordance with a conventional method. Presence of a band having a desired base chain length was confirmed in each of the 24 types of PCR products, and the production amount of each PCR product was determined

II. Preparation of DNA Microarray

(1) Design of Probe

Figure 5:
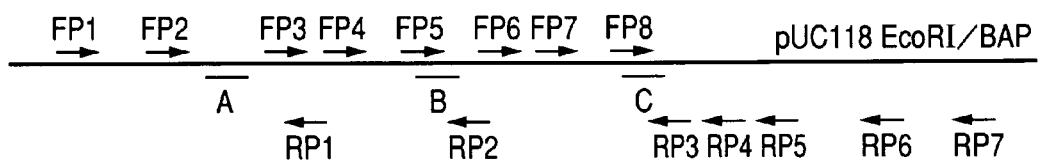
FIG. 5 shows the positional relationship between each of the primers and three probes to pUC118 EcoRI/BAP.

To detect 24 types of PCR products, probes were designed to 3 regions on pUC118 EcoRI/BAP. FIG. 5 shows probe regions on pUC118 EcoRI/BAP. Three probes were designed for three regions so as to be mutually different in chain length, that is, probes of 25-mers, 40-mers and 60-mers, were designed. The probes were designed in the same manner as in primers so as to specifically recognize a certain base sequence (target sequence) and to have the similar GC % and hybrid melting temperature (Tm).

Table 12 shows the name, base sequence and Tm value of each of the 9 types of designed probes.

TABLE 12

| Name | Sequence (5' → 3') | Tm value |
|---|---|---|
| A25 | ATG GTG CAC TCT CAG TAC AAT CTG G<br>SEQ ID NO: 22 | 75.7 |
| B25 | GTG GGT TAC ATC GAA CTC GAT CTC A<br>SEQ ID NO: 23 | 75.8 |
| C25 | GAT AAA GTT GCA GGA CCA CTT CTG C<br>SEQ ID NO: 24 | 75.7 |
| A40 | ATG GTG CAC TCT CAG TAC AAT CTG CTC TGA TGC CGC ATA G<br>SEQ ID NO: 25 | 80.7 |
| B40 | AGT TGG GTG CAC GAG TGG GTT ACA TCG AAC TGG ATC TCA A<br>SEQ ID NO: 26 | 80.9 |
| C40 | TAG ACT GGA TGG AGG CGG ATA AAG TTG CAG GAC CAC TTC T<br>SEQ ID NO: 27 | 80.8 |
| A60 | TTT TAT GGT GCA CTC TCA GTA CAA TCT GCT CTG ATG CCG CAT AGT TAA GCC AGC CCC GAC<br>SEQ ID NO: 28 | 83.3 |
| B60 | GTG GGT TAC ATC GAA CTG GAT CTC AAC AGC GGT AAG ATC TTG AGA GTT TTC GCC CCG AAA<br>SEQ ID NO: 29 | 83.3 |
| C60 | CTT CCC GGC AAC AAT TAA TAG ACT GGA TGG AGG CGG ATA AAG TTG CAG GAC CAC TTC TGC<br>SEQ ID NO: 30 | 83.3 |

Each of the aforementioned probes has a sequence on the same strand of pUC118 EcoRI/BAP as that the forward primer. Therefore, the sequence that hybridizes with each of the probes to form a double strand is that of a complementary strand extending from a reverse primer.

In the hybrid between each of the PCR products and the corresponding probe, the length of a target strand upstream of the hybrid region (L1) and the length downstream of the hybrid region (L2), and L1/L2 are shown in Tables below. Table 13 shows 25-mer probes, A25, B25 and C25, Table 14 40-mer probes, and Table 15 60-mer probes.

TABLE 13

| No. | Forward primer | Reverse primer | Probe | Length of PCR product | L1 (bp) | L2 (bp) | L1/L2 |
|---|---|---|---|---|---|---|---|
| 1 | FP1 | RP1 | A25 | 811 | 152 | 634 | 0.24 |
| 2 | FP1 | RP2 | A25 | 1336 | 677 | 634 | 1.07 |
| 3 | FP1 | RP2 | B25 | 1336 | 169 | 1142 | 0.15 |
| 4 | FP1 | RP4 | A25 | 1786 | 1127 | 634 | 1.78 |
| 5 | FP1 | RP4 | B25 | 1786 | 619 | 1142 | 0.54 |
| 6 | FP1 | RP4 | C25 | 1786 | 109 | 1652 | 0.07 |
| 7 | FP1 | RP6 | A25 | 2019 | 1360 | 634 | 2.15 |
| 8 | FP1 | RP6 | B25 | 2019 | 852 | 1142 | 0.75 |
| 9 | FP1 | RP6 | C25 | 2019 | 342 | 1652 | 0.21 |
| 10 | FP1 | RP7 | A25 | 2345 | 1686 | 634 | 2.66 |
| 11 | FP1 | RP7 | B25 | 2345 | 1178 | 1142 | 1.03 |
| 12 | FP1 | RP7 | C25 | 2345 | 668 | 1652 | 0.40 |
| 13 | FP2 | RP4 | A25 | 1398 | 1127 | 246 | 4.58 |
| 14 | FP2 | RP4 | B25 | 1398 | 619 | 754 | 0.82 |
| 15 | FP2 | RP4 | C25 | 1398 | 109 | 1264 | 0.09 |
| 16 | FP2 | RP7 | A25 | 1957 | 1686 | 246 | 6.85 |
| 17 | FP2 | RP7 | B25 | 1957 | 1178 | 754 | 1.56 |
| 18 | FP2 | RP7 | C25 | 1957 | 668 | 1264 | 0.53 |
| 19 | FP3 | RP4 | B25 | 1014 | 619 | 370 | 1.67 |
| 20 | FP3 | RP4 | C25 | 1014 | 109 | 880 | 0.12 |
| 21 | FP3 | RP6 | B25 | 1247 | 852 | 370 | 2.30 |
| 22 | FP3 | RP6 | C25 | 1247 | 342 | 880 | 0.39 |
| 23 | FP3 | RP7 | B25 | 1573 | 1178 | 370 | 3.18 |
| 24 | FP3 | RP7 | C25 | 1573 | 668 | 880 | 0.76 |
| 25 | FP4 | RP4 | B25 | 909 | 619 | 265 | 2.34 |
| 26 | FP4 | RP4 | C25 | 909 | 109 | 775 | 0.14 |
| 27 | FP5 | RP3 | B25 | 640 | 545 | 70 | 7.79 |
| 28 | FP5 | RP3 | C25 | 640 | 35 | 580 | 0.06 |
| 29 | FP5 | RP4 | B25 | 714 | 619 | 70 | 8.84 |
| 30 | FP5 | RP4 | C25 | 714 | 109 | 580 | 0.19 |
| 31 | FP6 | RP3 | C25 | 367 | 35 | 307 | 0.11 |
| 32 | FP6 | RP4 | C25 | 441 | 109 | 307 | 0.36 |
| 33 | FP6 | RP7 | C25 | 1000 | 668 | 307 | 2.18 |
| 34 | FP7 | RP3 | C25 | 190 | 35 | 130 | 0.27 |
| 35 | FP7 | RP4 | C25 | 264 | 109 | 130 | 0.84 |
| 36 | FP7 | RP5 | C25 | 305 | 150 | 130 | 1.15 |
| 37 | FP7 | RP6 | C25 | 497 | 342 | 130 | 2.63 |
| 38 | FP8 | RP3 | C25 | 104 | 35 | 44 | 0.80 |
| 39 | FP8 | RP4 | C25 | 178 | 109 | 44 | 2.48 |
| 40 | FP8 | RP5 | C25 | 219 | 150 | 44 | 3.41 |
| 41 | FP8 | RP6 | C25 | 411 | 342 | 44 | 7.77 |

TABLE 14

| No. | Forward primer | Reverse primer | Probe | Length of PCR product | L1 (bp) | L2 (bp) | L1/L2 |
|---|---|---|---|---|---|---|---|
| 1 | FP1 | RP1 | A40 | 811 | 137 | 634 | 0.22 |
| 2 | FP1 | RP2 | A40 | 1336 | 662 | 634 | 1.04 |
| 3 | FP1 | RP2 | B40 | 1336 | 168 | 1128 | 0.15 |
| 4 | FP1 | RP4 | A40 | 1786 | 1112 | 634 | 1.75 |
| 5 | FP1 | RP4 | B40 | 1786 | 618 | 1128 | 0.55 |
| 6 | FP1 | RP4 | C40 | 1786 | 111 | 1635 | 0.07 |
| 7 | FP1 | RP6 | A40 | 2019 | 1345 | 634 | 2.12 |
| 8 | FP1 | RP6 | B40 | 2019 | 851 | 1128 | 0.75 |
| 9 | FP1 | RP6 | C40 | 2019 | 344 | 1635 | 0.21 |
| 10 | FP1 | RP7 | A40 | 2345 | 1671 | 634 | 2.64 |
| 11 | FP1 | RP7 | B40 | 2345 | 1177 | 1128 | 1.04 |
| 12 | FP1 | RP7 | C40 | 2345 | 670 | 1635 | 0.41 |
| 13 | FP2 | RP4 | A40 | 1398 | 1112 | 246 | 4.52 |
| 14 | FP2 | RP4 | B40 | 1398 | 618 | 740 | 0.84 |
| 15 | FP2 | RP4 | C40 | 1398 | 111 | 1247 | 0.09 |
| 16 | FP2 | RP7 | A40 | 1957 | 1671 | 246 | 6.79 |
| 17 | FP2 | RP7 | B40 | 1957 | 1177 | 740 | 1.59 |
| 18 | FP2 | RP7 | C40 | 1957 | 670 | 1247 | 0.54 |
| 19 | FP3 | RP4 | B40 | 1014 | 618 | 356 | 1.74 |
| 20 | FP3 | RP4 | C40 | 1014 | 111 | 863 | 0.13 |
| 21 | FP3 | RP6 | B40 | 1247 | 851 | 356 | 2.39 |
| 22 | FP3 | RP6 | C40 | 1247 | 344 | 863 | 0.40 |
| 23 | FP3 | RP7 | B40 | 1573 | 1177 | 356 | 3.31 |
| 24 | FP3 | RP7 | C40 | 1573 | 670 | 863 | 0.78 |
| 25 | FP4 | RP4 | B40 | 909 | 618 | 251 | 2.46 |
| 26 | FP4 | RP4 | C40 | 909 | 111 | 758 | 0.15 |
| 27 | FP5 | RP3 | B40 | 640 | 545 | 70 | 7.79 |
| 28 | FP5 | RP3 | C40 | 640 | 37 | 563 | 0.07 |
| 29 | FP5 | RP4 | B40 | 714 | 618 | 56 | 11.04 |
| 30 | FP5 | RP4 | C40 | 714 | 111 | 563 | 0.20 |
| 31 | FP6 | RP3 | C40 | 367 | 37 | 290 | 0.13 |

TABLE 14-continued

| No. | Forward primer | Reverse primer | Probe | Length of PCR product | L1 (bp) | L2 (bp) | L1/L2 |
|---|---|---|---|---|---|---|---|
| 32 | FP6 | RP4 | C40 | 441 | 111 | 290 | 0.38 |
| 33 | FP6 | RP7 | C40 | 1000 | 670 | 290 | 2.31 |
| 34 | FP7 | RP3 | C40 | 190 | 37 | 113 | 0.33 |
| 35 | FP7 | RP4 | C40 | 264 | 111 | 113 | 0.98 |
| 36 | FP7 | RP5 | C40 | 305 | 152 | 113 | 1.35 |
| 37 | FP7 | RP6 | C40 | 497 | 344 | 113 | 3.04 |
| 38 | FP8 | RP3 | C40 | 104 | 37 | 27 | 1.37 |
| 39 | FP8 | RP4 | C40 | 178 | 111 | 27 | 4.11 |
| 40 | FP8 | RP5 | C40 | 219 | 152 | 27 | 5.63 |
| 41 | FP8 | RP6 | C40 | 411 | 344 | 27 | 12.74 |

TABLE 15

| No. | Forward primer | Reverse primer | Probe | Length of PCR product | L1 (bp) | L2 (bp) | L1/L2 |
|---|---|---|---|---|---|---|---|
| 1 | FP1 | RP1 | A60 | 811 | 115 | 636 | 0.18 |
| 2 | FP1 | RP2 | A60 | 1336 | 640 | 636 | 1.01 |
| 3 | FP1 | RP2 | B60 | 1336 | 148 | 1128 | 0.13 |
| 4 | FP1 | RP4 | A60 | 1786 | 1090 | 636 | 1.71 |
| 5 | FP1 | RP4 | B60 | 1786 | 598 | 1128 | 0.53 |
| 6 | FP1 | RP4 | C60 | 1786 | 91 | 1635 | 0.06 |
| 7 | FP1 | RP6 | A60 | 2019 | 1323 | 636 | 2.08 |
| 8 | FP1 | RP6 | B60 | 2019 | 831 | 1128 | 0.74 |
| 9 | FP1 | RP6 | C60 | 2019 | 324 | 1635 | 0.20 |
| 10 | FP1 | RP7 | A60 | 2345 | 1649 | 636 | 2.59 |
| 11 | FP1 | RP7 | B60 | 2345 | 1157 | 1128 | 1.03 |
| 12 | FP1 | RP7 | C60 | 2345 | 650 | 1635 | 0.40 |
| 13 | FP2 | RP4 | A60 | 1398 | 1090 | 248 | 4.40 |
| 14 | FP2 | RP4 | B60 | 1398 | 598 | 740 | 0.81 |
| 15 | FP2 | RP4 | C60 | 1398 | 91 | 1247 | 0.07 |
| 16 | FP2 | RP7 | A60 | 1957 | 1649 | 248 | 6.65 |
| 17 | FP2 | RP7 | B60 | 1957 | 1157 | 740 | 1.56 |
| 18 | FP2 | RP7 | C60 | 1957 | 650 | 1247 | 0.52 |
| 19 | FP3 | RP4 | B60 | 1014 | 598 | 356 | 1.68 |
| 20 | FP3 | RP4 | C60 | 1014 | 91 | 863 | 0.11 |
| 21 | FP3 | RP6 | B60 | 1247 | 831 | 356 | 2.33 |
| 22 | FP3 | RP6 | C60 | 1247 | 324 | 863 | 0.38 |
| 23 | FP3 | RP7 | B60 | 1573 | 1157 | 356 | 3.25 |
| 24 | FP3 | RP7 | C60 | 1573 | 650 | 863 | 0.75 |
| 25 | FP4 | RP4 | B60 | 909 | 598 | 251 | 2.38 |
| 26 | FP4 | RP4 | C60 | 909 | 91 | 758 | 0.12 |
| 27 | FP5 | RP3 | B60 | 640 | 524 | 56 | 9.36 |
| 28 | FP5 | RP3 | C60 | 640 | 17 | 563 | 0.03 |
| 29 | FP5 | RP4 | B60 | 714 | 598 | 56 | 10.68 |
| 30 | FP5 | RP4 | C60 | 714 | 91 | 563 | 0.16 |
| 31 | FP6 | RP3 | C60 | 367 | 17 | 290 | 0.06 |
| 32 | FP6 | RP4 | C60 | 441 | 91 | 290 | 0.31 |
| 33 | FP6 | RP7 | C60 | 1000 | 650 | 290 | 2.24 |
| 34 | FP7 | RP3 | C60 | 190 | 17 | 113 | 0.15 |
| 35 | FP7 | RP4 | C60 | 264 | 91 | 113 | 0.81 |
| 36 | FP7 | RP5 | C60 | 305 | 132 | 113 | 1.17 |
| 37 | FP7 | RP6 | C60 | 497 | 324 | 113 | 2.87 |
| 38 | FP8 | RP3 | C60 | 104 | 17 | 27 | 0.63 |
| 39 | FP8 | RP4 | C60 | 178 | 91 | 27 | 3.37 |
| 40 | FP8 | RP5 | C60 | 219 | 132 | 27 | 4.89 |
| 41 | FP8 | RP6 | C60 | 411 | 324 | 27 | 12.00 |

(2) Preparation of Microarray

The steps from probe synthesis to microarray preparation were performed in the same manner as in Example 1. In this Example, a microarray was prepared for each of 9 probes. Similarly to Example 1, 16 spots were fixed on a single microarray.

III. Hybridization Reaction

Using the DNA microarray prepared in Step II and 24 PCR amplification products prepared in Step I, 243 kinds of hybridization were performed on the microarrays as shown in Tables 13 to 15.

(1) Blocking of DNA Microarray

Blocking was performed by using BSA in the same manner as in Example 1.

(2) Preparation of Hybridization Solution

PCR products were prepared so as to have the same molar concentration. Hybridization solutions were prepared by using the PCR amplification product solutions so as to obtain final concentrations mentioned below.

<Hybridization Solution>

6×SSPE/10% formamide/0.05% SDS/PCR amplification product solution (6×SSPE contains 900 mM NaCl, 60 mM $NaH_2PO_4.H_2O$, and 6 mM EDTA, pH 7.4).

(3) Hybridization

The microarray dewatered was placed in a hybridization apparatus (Hybridization Station, manufactured by Genomic Solutions Inc.) and hybridization was performed using the hybridization solution of the aforementioned composition in accordance with the conditions and procedure described below.

<Conditions and Procedure of Hybridization>

The hybridization solution was added to a microarray at 65° C., allowed to stand at 92° C. for 2 minutes, and then at 55° C. for 4 hours. Thereafter, the microarray was washed with 2×SSC and 0.1% SDS at 25° C., further washed with 2×SSC at 20° C., optionally rinsed with pure water in accordance with a conventional manual, and finally dewatered by a spin drier to dry.

TABLE 16

| Operation | Operation procedure/conditions |
|---|---|
| Addition | Hybridization solution is added at 65° C. |
| Reaction | 92° C. 2 minutes → 55° C. 4 hours |
| Wash | 2 × SSC/0.1% SDS at 25° C. |
| | 2 × SSC at 20° C. |
| (Rinse) | $H_2O$(manual rinse) |
| Dry | Spin dry |

(4) Fluorescence Measurement

After completion of the hybridization reaction, fluorescence was measured in the same manner as in Example 1. The fluorescent intensity values of individual PCR products are shown in Tables 17 to 19, which correspond to 25 mer, 40 mer, and 60 mer probes, respectively. Fluorescent intensity was calculated in the same manner as in Example 1.

TABLE 17

| No. | Forward primer | Reverse primer | Probe | Length of PCR product | L1 (bp) | L2 (bp) | L1/L2 | Fluorescent intensity |
|---|---|---|---|---|---|---|---|---|
| 1 | FP1 | RP1 | A25 | 811 | 152 | 634 | 0.24 | 3172.0 |
| 2 | FP1 | RP2 | A25 | 1336 | 677 | 634 | 1.07 | 52.4 |
| 3 | FP1 | RP2 | B25 | 1336 | 169 | 1142 | 0.15 | 3638.8 |
| 4 | FP1 | RP4 | A25 | 1786 | 1127 | 634 | 1.78 | 2.2 |
| 5 | FP1 | RP4 | B25 | 1786 | 619 | 1142 | 0.54 | 3077.4 |
| 6 | FP1 | RP4 | C25 | 1786 | 109 | 1652 | 0.07 | 3519.9 |
| 7 | FP1 | RP6 | A25 | 2019 | 1360 | 634 | 2.15 | 0.6 |
| 8 | FP1 | RP6 | B25 | 2019 | 852 | 1142 | 0.75 | 3020.5 |
| 9 | FP1 | RP6 | C25 | 2019 | 342 | 1652 | 0.21 | 3449.8 |
| 10 | FP1 | RP7 | A25 | 2345 | 1686 | 634 | 2.66 | 1.6 |
| 11 | FP1 | RP7 | B25 | 2345 | 1178 | 1142 | 1.03 | 722.5 |
| 12 | FP1 | RP7 | C25 | 2345 | 668 | 1652 | 0.40 | 2252.7 |
| 13 | FP2 | RP4 | A25 | 1398 | 1127 | 246 | 4.58 | 1.5 |
| 14 | FP2 | RP4 | B25 | 1398 | 619 | 754 | 0.82 | 2202.0 |
| 15 | FP2 | RP4 | C25 | 1398 | 109 | 1264 | 0.09 | 2762.2 |
| 16 | FP2 | RP7 | A25 | 1957 | 1686 | 246 | 6.85 | 1.4 |
| 17 | FP2 | RP7 | B25 | 1957 | 1178 | 754 | 1.56 | 24.1 |
| 18 | FP2 | RP7 | C25 | 1957 | 668 | 1264 | 0.53 | 1951.8 |
| 19 | FP3 | RP4 | B25 | 1014 | 619 | 370 | 1.67 | 22.4 |

TABLE 17-continued

| No. | Forward primer | Reverse primer | Probe | Length of PCR product | L1 (bp) | L2 (bp) | L1/L2 | Fluorescent intensity |
|---|---|---|---|---|---|---|---|---|
| 20 | FP3 | RP4 | C25 | 1014 | 109 | 880 | 0.12 | 2763.2 |
| 21 | FP3 | RP6 | B25 | 1247 | 852 | 370 | 2.30 | 0.5 |
| 22 | FP3 | RP6 | C25 | 1247 | 342 | 880 | 0.39 | 2203.1 |
| 23 | FP3 | RP7 | B25 | 1573 | 1178 | 370 | 3.18 | 0.5 |
| 24 | FP3 | RP7 | C25 | 1573 | 668 | 880 | 0.76 | 519.7 |
| 25 | FP4 | RP4 | B25 | 909 | 619 | 265 | 2.34 | 1.8 |
| 26 | FP4 | RP4 | C25 | 909 | 109 | 775 | 0.14 | 1893.2 |
| 27 | FP5 | RP3 | B25 | 640 | 545 | 70 | 7.79 | 1.1 |
| 28 | FP5 | RP3 | C25 | 640 | 35 | 580 | 0.06 | 2009.7 |
| 29 | FP5 | RP4 | B25 | 714 | 619 | 70 | 8.84 | 1.6 |
| 30 | FP5 | RP4 | C25 | 714 | 109 | 580 | 0.19 | 1388.6 |
| 31 | FP6 | RP3 | C25 | 367 | 35 | 307 | 0.11 | 1338.6 |
| 32 | FP6 | RP4 | C25 | 441 | 109 | 307 | 0.36 | 484.5 |
| 33 | FP6 | RP7 | C25 | 1000 | 668 | 307 | 2.18 | 1.3 |
| 34 | FP7 | RP3 | C25 | 190 | 35 | 130 | 0.27 | 590.1 |
| 35 | FP7 | RP4 | C25 | 264 | 109 | 130 | 0.84 | 73.4 |
| 36 | FP7 | RP5 | C25 | 305 | 150 | 130 | 1.15 | 167.3 |
| 37 | FP7 | RP6 | C25 | 497 | 342 | 130 | 2.63 | 2.7 |
| 38 | FP8 | RP3 | C25 | 104 | 35 | 44 | 0.80 | 797.2 |
| 39 | FP8 | RP4 | C25 | 178 | 109 | 44 | 2.48 | 709.4 |
| 40 | FP8 | RP5 | C25 | 219 | 150 | 44 | 3.41 | 643.4 |
| 41 | FP8 | RP6 | C25 | 411 | 342 | 44 | 7.77 | 3.1 |

TABLE 18

| No. | Forward primer | Reverse primer | Probe | Length of PCR product | L1 (bp) | L2 (bp) | L1/L2 | Fluorescent intensity |
|---|---|---|---|---|---|---|---|---|
| 1 | FP1 | RP1 | A40 | 811 | 137 | 634 | 0.22 | 6310.5 |
| 2 | FP1 | RP2 | A40 | 1336 | 662 | 634 | 1.04 | 466.2 |
| 3 | FP1 | RP2 | B40 | 1336 | 168 | 1128 | 0.15 | 7415.4 |
| 4 | FP1 | RP4 | A40 | 1786 | 1112 | 634 | 1.75 | 10.0 |
| 5 | FP1 | RP4 | B40 | 1786 | 618 | 1128 | 0.55 | 6451.3 |
| 6 | FP1 | RP4 | C40 | 1786 | 111 | 1635 | 0.07 | 8547.4 |
| 7 | FP1 | RP6 | A40 | 2019 | 1345 | 634 | 2.12 | 4.8 |
| 8 | FP1 | RP6 | B40 | 2019 | 851 | 1128 | 0.75 | 5920.8 |
| 9 | FP1 | RP6 | C40 | 2019 | 344 | 1635 | 0.21 | 8037.6 |
| 10 | FP1 | RP7 | A40 | 2345 | 1671 | 634 | 2.64 | 3.0 |
| 11 | FP1 | RP7 | B40 | 2345 | 1177 | 1128 | 1.04 | 1942.1 |
| 12 | FP1 | RP7 | C40 | 2345 | 670 | 1635 | 0.41 | 6506.2 |
| 13 | FP2 | RP4 | A40 | 1398 | 1112 | 246 | 4.52 | 3.2 |
| 14 | FP2 | RP4 | B40 | 1398 | 618 | 740 | 0.84 | 5026.4 |
| 15 | FP2 | RP4 | C40 | 1398 | 111 | 1247 | 0.09 | 7090.1 |
| 16 | FP2 | RP7 | A40 | 1957 | 1671 | 246 | 6.79 | 3.7 |
| 17 | FP2 | RP7 | B40 | 1957 | 1177 | 740 | 1.59 | 121.1 |
| 18 | FP2 | RP7 | C40 | 1957 | 670 | 1247 | 0.54 | 5571.0 |
| 19 | FP3 | RP4 | B40 | 1014 | 618 | 356 | 1.74 | 105.6 |
| 20 | FP3 | RP4 | C40 | 1014 | 111 | 863 | 0.13 | 7291.5 |
| 21 | FP3 | RP6 | B40 | 1247 | 851 | 356 | 2.39 | 4.0 |
| 22 | FP3 | RP6 | C40 | 1247 | 344 | 863 | 0.40 | 6122.6 |
| 23 | FP3 | RP7 | B40 | 1573 | 1177 | 356 | 3.31 | 0.5 |
| 24 | FP3 | RP7 | C40 | 1573 | 670 | 863 | 0.78 | 1967.1 |
| 25 | FP4 | RP4 | B40 | 909 | 618 | 251 | 2.46 | 19.9 |
| 26 | FP4 | RP4 | C40 | 909 | 111 | 758 | 0.15 | 5674.5 |
| 27 | FP5 | RP3 | B40 | 640 | 545 | 70 | 7.79 | 3.5 |
| 28 | FP5 | RP3 | C40 | 640 | 37 | 563 | 0.07 | 4904.3 |
| 29 | FP5 | RP4 | B40 | 714 | 618 | 56 | 11.04 | 4.0 |
| 30 | FP5 | RP4 | C40 | 714 | 111 | 563 | 0.20 | 4248.7 |
| 31 | FP6 | RP3 | C40 | 367 | 37 | 290 | 0.13 | 3611.1 |
| 32 | FP6 | RP4 | C40 | 441 | 111 | 290 | 0.38 | 1810.2 |
| 33 | FP6 | RP7 | C40 | 1000 | 670 | 290 | 2.31 | 7.4 |
| 34 | FP7 | RP3 | C40 | 190 | 37 | 113 | 0.33 | 1390.3 |
| 35 | FP7 | RP4 | C40 | 264 | 111 | 113 | 0.98 | 334.4 |
| 36 | FP7 | RP5 | C40 | 305 | 152 | 113 | 1.35 | 579.7 |
| 37 | FP7 | RP6 | C40 | 497 | 344 | 113 | 3.04 | 13.7 |
| 38 | FP8 | RP3 | C40 | 104 | 37 | 27 | 1.37 | 1434.0 |
| 39 | FP8 | RP4 | C40 | 178 | 111 | 27 | 4.11 | 1674.2 |
| 40 | FP8 | RP5 | C40 | 219 | 152 | 27 | 5.63 | 1737.6 |
| 41 | FP8 | RP6 | C40 | 411 | 344 | 27 | 12.74 | 14.6 |

TABLE 19

| No. | Forward primer | Reverse primer | Probe | Length of PCR product | L1 (bp) | L2 (bp) | L1/L2 | Fluorescent intensity |
|---|---|---|---|---|---|---|---|---|
| 1 | FP1 | RP1 | A60 | 811 | 115 | 636 | 0.18 | 9191.0 |
| 2 | FP1 | RP2 | A60 | 1336 | 640 | 636 | 1.01 | 1963.3 |
| 3 | FP1 | RP2 | B60 | 1336 | 148 | 1128 | 0.13 | 10343.4 |
| 4 | FP1 | RP4 | A60 | 1786 | 1090 | 636 | 1.71 | 42.7 |
| 5 | FP1 | RP4 | B60 | 1786 | 598 | 1128 | 0.53 | 11856.1 |
| 6 | FP1 | RP4 | C60 | 1786 | 91 | 1635 | 0.06 | 10930.5 |
| 7 | FP1 | RP6 | A60 | 2019 | 1323 | 636 | 2.08 | 10.7 |
| 8 | FP1 | RP6 | B60 | 2019 | 831 | 1128 | 0.74 | 11330.2 |
| 9 | FP1 | RP6 | C60 | 2019 | 324 | 1635 | 0.20 | 11745.8 |
| 10 | FP1 | RP7 | A60 | 2345 | 1649 | 636 | 2.59 | 5.3 |
| 11 | FP1 | RP7 | B60 | 2345 | 1157 | 1128 | 1.03 | 5436.4 |
| 12 | FP1 | RP7 | C60 | 2345 | 650 | 1635 | 0.40 | 10108.0 |
| 13 | FP2 | RP4 | A60 | 1398 | 1090 | 248 | 4.40 | 10.9 |
| 14 | FP2 | RP4 | B60 | 1398 | 598 | 740 | 0.81 | 9617.4 |
| 15 | FP2 | RP4 | C60 | 1398 | 91 | 1247 | 0.07 | 9193.6 |
| 16 | FP2 | RP7 | A60 | 1957 | 1649 | 248 | 6.65 | 7.6 |
| 17 | FP2 | RP7 | B60 | 1957 | 1157 | 740 | 1.56 | 826.5 |
| 18 | FP2 | RP7 | C60 | 1957 | 650 | 1247 | 0.52 | 8783.0 |
| 19 | FP3 | RP4 | B60 | 1014 | 598 | 356 | 1.68 | 1061.5 |
| 20 | FP3 | RP4 | C60 | 1014 | 91 | 863 | 0.11 | 9409.1 |
| 21 | FP3 | RP6 | B60 | 1247 | 831 | 356 | 2.33 | 44.6 |
| 22 | FP3 | RP6 | C60 | 1247 | 324 | 863 | 0.38 | 9139.9 |
| 23 | FP3 | RP7 | B60 | 1573 | 1157 | 356 | 3.25 | 0.8 |
| 24 | FP3 | RP7 | C60 | 1573 | 650 | 863 | 0.75 | 3470.7 |
| 25 | FP4 | RP4 | B60 | 909 | 598 | 251 | 2.38 | 306.8 |
| 26 | FP4 | RP4 | C60 | 909 | 91 | 758 | 0.12 | 7428.8 |
| 27 | FP5 | RP3 | B60 | 640 | 524 | 56 | 9.36 | 9.1 |
| 28 | FP5 | RP3 | C60 | 640 | 17 | 563 | 0.03 | 5929.9 |
| 29 | FP5 | RP4 | B60 | 714 | 598 | 56 | 10.68 | 11.9 |
| 30 | FP5 | RP4 | C60 | 714 | 91 | 563 | 0.16 | 6037.3 |
| 31 | FP6 | RP3 | C60 | 367 | 17 | 290 | 0.06 | 5069.8 |
| 32 | FP6 | RP4 | C60 | 441 | 91 | 290 | 0.31 | 2892.6 |
| 33 | FP6 | RP7 | C60 | 1000 | 650 | 290 | 2.24 | 15.4 |
| 34 | FP7 | RP3 | C60 | 190 | 17 | 113 | 0.15 | 2119.3 |
| 35 | FP7 | RP4 | C60 | 264 | 91 | 113 | 0.81 | 649.6 |
| 36 | FP7 | RP5 | C60 | 305 | 132 | 113 | 1.17 | 1108.0 |
| 37 | FP7 | RP6 | C60 | 497 | 324 | 113 | 2.87 | 37.4 |
| 38 | FP8 | RP3 | C60 | 104 | 17 | 27 | 0.63 | 1448.2 |
| 39 | FP8 | RP4 | C60 | 178 | 91 | 27 | 3.37 | 2060.3 |
| 40 | FP8 | RP5 | C60 | 219 | 132 | 27 | 4.89 | 2130.9 |
| 41 | FP8 | RP6 | C60 | 411 | 324 | 27 | 12.00 | 59.8 |

IV. Analysis of Results

Figure 6:
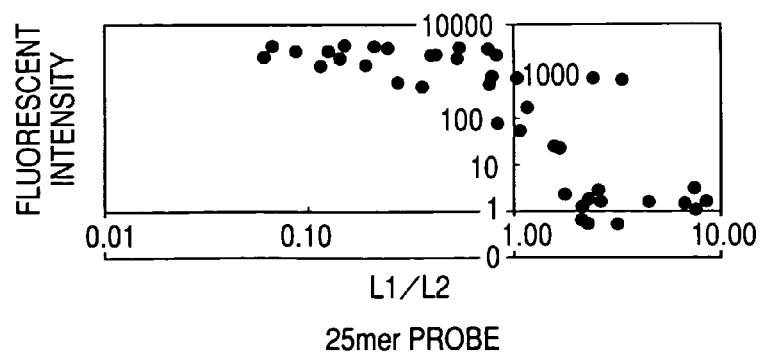
FIG. 6 is a graph plotting fluorescent intensity to L1/L2 value in the case of a 25-mer probe.
Figure 7:
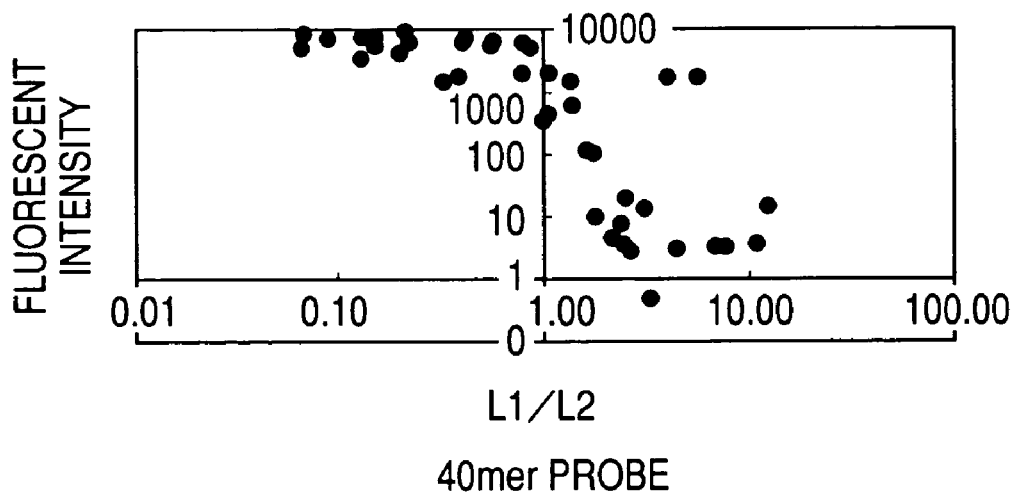
FIG. 7 is a graph plotting fluorescent intensity to L1/L2 value in the case of a 40-mer probe.
Figure 8:
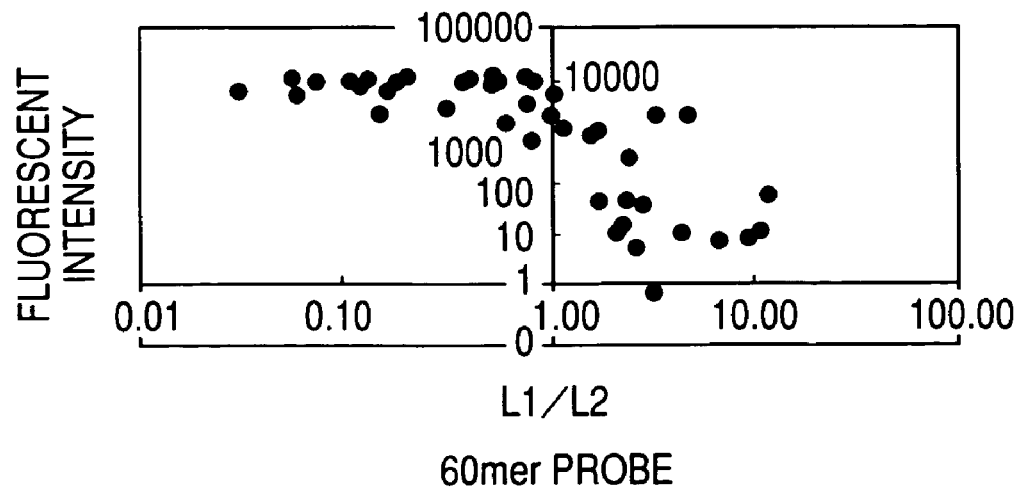
FIG. 8 is a graph plotting fluorescent intensity to L1/L2 value in the case of a 60-mer probe.

Based on the results, graphs were made by plotting fluorescent intensity to L1/L2 value. To facilitate understanding, the vertical and horizontal axes are graduated logarithmically. FIGS. 6, 7 and 8 show the cases of 25-met, 40-mer and 60-mer probes, respectively.

From the results above, even when the same sample in the same concentration was reacted with the probes designed to have the same length and virtually the same Tm value, the fluorescent intensities of the probes greatly differ. This means the stability of hybrids greatly differs. It was found out that if the L1/L2 value falls within the range of 0 to 1.5, a high fluorescent value was obtained, and thus a stable hybrid was obtained. If the L1/L2 value ranges from 0 to 1, the hybrid is particularly stable. In contrast, if the L1/L2 value is 2 or more, fluorescent intensity was extremely low with several exceptions, and the resultant hybrid had an extremely low stability.

Example 3

(1) Design of Probe

Of nine probes designed in Example 2, three types of 25-mer probes were modified to have a thiol group at the 3' end. A thiol group was introduced only to the 3' end and not to the 5' end.

Table 20 shows the name, base sequence, and Tm value of each of the three types of probes.

TABLE 20

| Name | Sequence (5' → 3') | Tm value |
|---|---|---|
| AR25 | ATGGTGCACTGTGAGTAGAATGTGC<br>SEQ ID NO: 24 | 75.7 |
| BR25 | GTGGGTTAGATGGAACTGGATGTGA<br>SEQ ID NO: 25 | 75.8 |
| CR25 | GATAAAGTTGCAGGAGCAGTTbTGG<br>SEQ ID NO: 26 | 75.7 |

The same as in Example 2, the sequence that hybridizes with each of the probes to form a hybrid is the complementary strand extending from a reverse primer.

Figure 9:
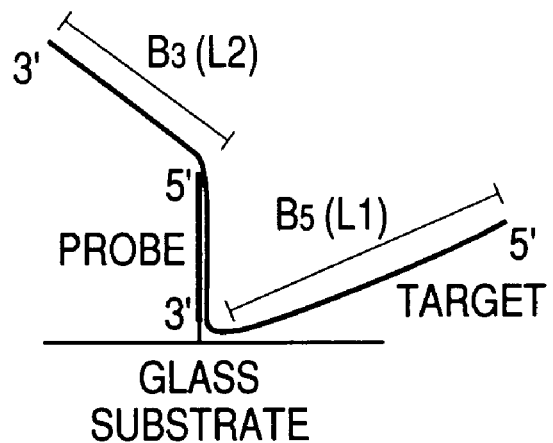
FIG. 9 shows an illustration of a hybrid between a probe immobilized at the 3' end and a target strand and the positional relationship between L1 and L2.

An example of hybrids formed between each of the PCR products (target strand) synthesized in Example 2 and each of the three probes synthesized herein, is shown in FIG. 9, where the length of a target strand upstream the hybridized region is represented by $B_5$ (L1) and that downstream the hybridized region is represented by $B_3$ (L2) The values of L1, L2 and L1/L2 with respect to each of the PCR products synthesized in Example 2 are shown in Table 21. Since a probe and each of PCR products (target strand) have the same positional relationship, the values of L1, L2 and L1/L2 are the same as in Example 2.

TABLE 21

| No. | Forward primer | Reverse primer | Probe | Length of PCR product | L1 (bp) | L2 (bp) | L1/L2 |
|---|---|---|---|---|---|---|---|
| 1 | FP1 | RP1 | AR25 | 811 | 152 | 634 | 0.24 |
| 2 | FP1 | RP2 | AR25 | 1336 | 677 | 634 | 1.07 |
| 3 | FP1 | RP2 | BR25 | 1336 | 169 | 1142 | 0.15 |
| 4 | FP1 | RP4 | AR25 | 1786 | 1127 | 634 | 1.78 |
| 5 | FP1 | RP4 | BR25 | 1786 | 619 | 1142 | 0.54 |
| 6 | FP1 | RP4 | CR25 | 1786 | 109 | 1652 | 0.07 |
| 7 | FP1 | RP6 | AR25 | 2019 | 1360 | 634 | 2.15 |
| 8 | FP1 | RP6 | BR25 | 2019 | 852 | 1142 | 0.75 |
| 9 | FP1 | RP6 | CR25 | 2019 | 342 | 1652 | 0.21 |
| 10 | FP1 | RP7 | AR25 | 2345 | 1686 | 634 | 2.66 |
| 11 | FP1 | RP7 | BR25 | 2345 | 1178 | 1142 | 1.03 |
| 12 | FP1 | RP7 | CR25 | 2345 | 668 | 1652 | 0.40 |
| 13 | FP2 | RP4 | AR25 | 1398 | 1127 | 246 | 4.58 |
| 14 | FP2 | RP4 | BR25 | 1398 | 619 | 754 | 0.82 |
| 15 | FP2 | RP4 | CR25 | 1398 | 109 | 1264 | 0.09 |
| 16 | FP2 | RP7 | AR25 | 1957 | 1686 | 246 | 6.85 |
| 17 | FP2 | RP7 | BR25 | 1957 | 1178 | 754 | 1.56 |
| 18 | FP2 | RP7 | CR25 | 1957 | 668 | 1264 | 0.53 |
| 19 | FP3 | RP4 | BR25 | 1014 | 619 | 370 | 1.67 |
| 20 | FP3 | RP4 | CR25 | 1014 | 109 | 880 | 0.12 |
| 21 | FP3 | RP6 | BR25 | 1247 | 852 | 370 | 2.30 |
| 22 | FP3 | RP6 | CR25 | 1247 | 342 | 880 | 0.39 |
| 23 | FP3 | RP7 | BR25 | 1573 | 1178 | 370 | 3.18 |
| 24 | FP3 | RP7 | CR25 | 1573 | 668 | 880 | 0.76 |
| 25 | FP4 | RP4 | BR25 | 909 | 619 | 265 | 2.34 |
| 26 | FP4 | RP4 | CR25 | 909 | 109 | 775 | 0.14 |
| 27 | FP5 | RP3 | BR25 | 640 | 545 | 70 | 7.79 |
| 28 | FP5 | RP3 | CR25 | 640 | 35 | 580 | 0.06 |
| 29 | FP5 | RP4 | BR25 | 714 | 619 | 70 | 8.84 |
| 30 | FP5 | RP4 | CR25 | 714 | 109 | 580 | 0.19 |
| 31 | FP6 | RP3 | CR25 | 367 | 35 | 307 | 0.11 |
| 32 | FP6 | RP4 | CR25 | 441 | 109 | 307 | 0.36 |
| 33 | FP6 | RP7 | CR25 | 1000 | 668 | 307 | 2.18 |
| 34 | FP7 | RP3 | CR25 | 190 | 35 | 130 | 0.27 |
| 35 | FP7 | RP4 | CR25 | 264 | 109 | 130 | 0.84 |
| 36 | FP7 | RP5 | CR25 | 305 | 150 | 130 | 1.15 |
| 37 | FP7 | RP6 | CR25 | 497 | 342 | 130 | 2.63 |
| 38 | FP8 | RP3 | CR25 | 104 | 35 | 44 | 0.80 |
| 39 | FP8 | RP4 | CR25 | 178 | 109 | 44 | 2.48 |
| 40 | FP8 | RP5 | CR25 | 219 | 150 | 44 | 3.41 |
| 41 | FP8 | RP6 | CR25 | 411 | 342 | 44 | 7.77 |

(2) Preparation of Microarray

A DNA microarray was prepared for each of three probes in the same manner as in Example 2 and 16 spots were fixed on a single DNA microarray.

(3) Hybridization Reaction and Measurement of Fluorescence

Hybridization reaction was performed and then fluorescence was measured in the same manner as in Example 2. The fluorescent intensity values obtained from individual microarrays are shown in Table 22.

TABLE 22

| No. | Forward primer | Reverse primer | Probe | Length of PCR product | L1 (bp) | L2 (bp) | L1/L2 | Fluorescent intensity |
|---|---|---|---|---|---|---|---|---|
| 1 | FP1 | RP1 | AR25 | 811 | 152 | 634 | 0.24 | 2569.3 |
| 2 | FP1 | RP2 | AR25 | 1336 | 677 | 634 | 1.07 | 54.0 |
| 3 | FP1 | RP2 | BR25 | 1336 | 169 | 1142 | 0.15 | 3056.6 |
| 4 | FP1 | RP4 | AR25 | 1786 | 1127 | 634 | 1.78 | 1.8 |
| 5 | FP1 | RP4 | BR25 | 1786 | 619 | 1142 | 0.54 | 2277.3 |
| 6 | FP1 | RP4 | CR25 | 1786 | 109 | 1652 | 0.07 | 3379.1 |
| 7 | FP1 | RP6 | AR25 | 2019 | 1360 | 634 | 2.15 | 0.5 |
| 8 | FP1 | RP6 | BR25 | 2019 | 852 | 1142 | 0.75 | 2476.8 |
| 9 | FP1 | RP6 | CR25 | 2019 | 342 | 1652 | 0.21 | 2207.9 |
| 10 | FP1 | RP7 | AR25 | 2345 | 1686 | 634 | 2.66 | 1.4 |
| 11 | FP1 | RP7 | BR25 | 2345 | 1178 | 1142 | 1.03 | 556.3 |
| 12 | FP1 | RP7 | CR25 | 2345 | 668 | 1652 | 0.40 | 1667.0 |
| 13 | FP2 | RP4 | AR25 | 1398 | 1127 | 246 | 4.58 | 1.3 |
| 14 | FP2 | RP4 | BR25 | 1398 | 619 | 754 | 0.82 | 1431.3 |
| 15 | FP2 | RP4 | CR25 | 1398 | 109 | 1264 | 0.09 | 2679.3 |
| 16 | FP2 | RP7 | AR25 | 1957 | 1686 | 246 | 6.85 | 1.2 |
| 17 | FP2 | RP7 | BR25 | 1957 | 1178 | 754 | 1.56 | 49.8 |
| 18 | FP2 | RP7 | CR25 | 1957 | 668 | 1264 | 0.53 | 1678.5 |
| 19 | FP3 | RP4 | BR25 | 1014 | 619 | 370 | 1.67 | 18.8 |
| 20 | FP3 | RP4 | CR25 | 1014 | 109 | 880 | 0.12 | 2321.1 |
| 21 | FP3 | RP6 | BR25 | 1247 | 852 | 370 | 2.30 | 0.0 |
| 22 | FP3 | RP6 | CR25 | 1247 | 342 | 880 | 0.39 | 2137.0 |
| 23 | FP3 | RP7 | BR25 | 1573 | 1178 | 370 | 3.18 | 0.4 |
| 24 | FP3 | RP7 | CR25 | 1573 | 668 | 880 | 0.76 | 556.0 |
| 25 | FP4 | RP4 | BR25 | 909 | 619 | 265 | 2.34 | 3.7 |
| 26 | FP4 | RP4 | CR25 | 909 | 109 | 775 | 0.14 | 1666.0 |
| 27 | FP5 | RP3 | BR25 | 640 | 545 | 70 | 7.79 | 0.8 |
| 28 | FP5 | RP3 | CR25 | 640 | 35 | 580 | 0.06 | 1748.5 |
| 29 | FP5 | RP4 | BR25 | 714 | 619 | 70 | 8.84 | 0.1 |
| 30 | FP5 | RP4 | CR25 | 714 | 109 | 580 | 0.19 | 1222.0 |
| 31 | FP6 | RP3 | CR25 | 367 | 35 | 307 | 0.11 | 1030.7 |
| 32 | FP6 | RP4 | CR25 | 441 | 109 | 307 | 0.36 | 382.8 |
| 33 | FP6 | RP7 | CR25 | 1000 | 668 | 307 | 2.18 | 1.1 |
| 34 | FP7 | RP3 | CR25 | 190 | 35 | 130 | 0.27 | 454.4 |
| 35 | FP7 | RP4 | CR25 | 264 | 109 | 130 | 0.84 | 67.6 |
| 36 | FP7 | RP5 | CR25 | 305 | 150 | 130 | 1.15 | 140.6 |
| 37 | FP7 | RP6 | CR25 | 497 | 342 | 130 | 2.63 | 2.9 |
| 38 | FP8 | RP3 | CR25 | 104 | 35 | 44 | 0.80 | 693.5 |
| 39 | FP8 | RP4 | CR25 | 178 | 109 | 44 | 2.48 | 524.9 |
| 40 | FP8 | RP5 | CR25 | 219 | 150 | 44 | 3.41 | 540.4 |
| 41 | FP8 | RP6 | CR25 | 411 | 342 | 44 | 7.77 | 4.8 |

(4) Analysis of Results

Figure 10:
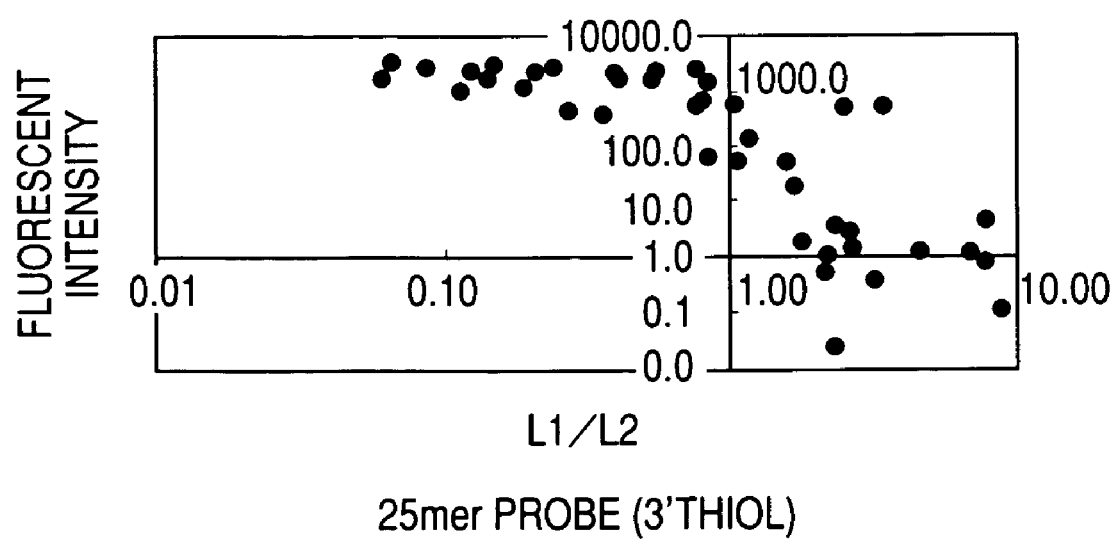
FIG. 10 is a graph plotting fluorescent intensity to L1/L2 value in a 25-mer probe immobilized at the 3' end.

A graph was made by plotting fluorescent intensity to L1/L2 value in the same manner as in Example 2 and shown in FIG. 10. In this Example also the vertical and horizontal axes are graduated logarithmically. As is apparent from this graph, high fluorescent values are obtained at an L1/L2 value from 0 to 1.5. It was clearly demonstrated that stable hybrids were obtained. The high intensity is remarkably obtained especially at an L1/L2 value from 0 to 1.

The results demonstrate that a stable hybrid is also formed, depending upon the relationship between L1 and L2, even when a probe immobilized at the 3' end through a thiol group, the same as the case immobilized at the 5' end. Hence, no matter what type of immobilization method is employed, a stable hybrid can be obtained according to the present invention.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2003-324647 filed on Sep. 17, 2003, which is hereby incorporated by reference herein.

What is claimed is:

1. A method for designing a nucleic acid probe set comprising more than one probe nucleic acid immobilized on a substrate for hybridizing with target sequences in target strands of sample nucleic acids, said method comprising:
   confirming that 70% or more of the probes on the substrate satisfy the following conditions when the probes hybridize to the sample nucleic acids:
   the probe nucleic acid is shorter than the target strand;
   the sample nucleic acid and a complementary probe sequence are present in the hybrid; and
   $L1 \leq L2$, wherein L1 is the number of bases of a 5' portion of the target strand not being the target sequence, L2 is the number of bases of a 3' portion of the target strand not being the target sequence, and each of L1 and L2 is greater than 0.

2. A method for designing a nucleic acid probe set comprising more than one probe nucleic acid immobilized on a substrate for hybridizing with target sequences in target strands of sample nucleic acids, said method comprising:
   confirming that 70% or more of the probes on the substrate satisfy the following conditions (1) and (2):
   (1) the hybrid is formed between a target sequence present in a target strand of the sample nucleic acid and a complementary probe sequence present in the probe set; and
   (2) the target strand of the sample nucleic acid is longer than the probe nucleic acid and $L1 \leq L2$, wherein L1 is the number of bases of a 5' portion of the target strand not being the target sequence, L2 is the number of bases of a 3' portion of the target strand not being the target sequence, and each of L1 and L2 is greater than 0.

* * * * *